United States Patent
Reid et al.

(10) Patent No.: US 11,401,549 B2
(45) Date of Patent: Aug. 2, 2022

(54) ANALYSIS OF A POLYMER

(71) Applicant: Oxford Nanopore Technologies PLC, Oxford (GB)

(72) Inventors: Stuart William Reid, Oxford (GB); Gavin Harper, Sonning (GB); Clive Gavin Brown, Cambridge (GB); Daniel John Turner, Oxford (GB); Andrew John Heron, Oxford (GB); Christopher James Wright, London (GB)

(73) Assignee: Oxford Nanopore Technologies PLC, Oxford (GB)

( * ) Notice: Subject to any disclaimer, the term of this patent is extended or adjusted under 35 U.S.C. 154(b) by 0 days.

(21) Appl. No.: 15/930,198

(22) Filed: May 12, 2020

(65) Prior Publication Data
US 2021/0079460 A1    Mar. 18, 2021

Related U.S. Application Data

(63) Continuation of application No. 15/519,325, filed as application No. PCT/GB2015/053083 on Oct. 16, 2015, now Pat. No. 10,689,697.

(30) Foreign Application Priority Data

Oct. 16, 2014 (GB) .................... 1418366
Oct. 16, 2014 (GB) .................... 1418379
May 6, 2015 (GB) .................... 1507742

(51) Int. Cl.
*C12Q 1/6869* (2018.01)
*G16B 30/00* (2019.01)
(Continued)

(52) U.S. Cl.
CPC ..... *C12Q 1/6869* (2013.01); *G01N 33/48721* (2013.01); *G16B 30/00* (2019.02); *G16B 30/10* (2019.02)

(58) Field of Classification Search
CPC ...... C12Q 1/6869; G16B 30/10; G16B 30/00; G01N 33/48721
See application file for complete search history.

(56) References Cited

U.S. PATENT DOCUMENTS 5,795,782 A   8/1998  Church et al.
6,128,587 A   10/2000 Sjolander
(Continued)

FOREIGN PATENT DOCUMENTS

EP   1351183 A2   10/2003
EP   1544310 A2   6/2005
(Continued)

OTHER PUBLICATIONS

International Search Report and Written Opinion, for Application No. PCT/GB2015/053083, dated Mar. 30, 2016.
(Continued)

*Primary Examiner* — Narayan K Bhat
(74) *Attorney, Agent, or Firm* — Wolf, Greenfield & Sacks, P.C.

(57) ABSTRACT

A biochemical analysis system analyses polymers by taking measurements of a polymer from a sensor element comprising a nanopore during translocation of the polymer through the nanopore. When a polymer has partially translocated, the series of measurements is analysed using reference data derived from a reference sequence to provide a measure of similarity. Responsive to the measure of similarity, the sensor element may be selectively operated to eject the polymer and thereby make the nanopore available to receive a further polymer. Where the biochemical analysis system
(Continued)

comprises an array of sensor elements and is takes measurements from sensor elements selected in a multiplexed manner, responsive to the measure of similarity, the biochemical analysis system ceases taking measurements from the currently selected sensor element and to starts taking measurements from a newly selected sensor element.

9 Claims, 11 Drawing Sheets

Specification includes a Sequence Listing.

(51) Int. Cl.
    *G01N 33/487*     (2006.01)
    *G16B 30/10*     (2019.01)

(56) References Cited

U.S. PATENT DOCUMENTS

| | | |
|---|---|---|
| 7,625,706 B2 | 12/2009 | Akeson et al. |
| 7,731,826 B2 | 6/2010 | Hibbs et al. |
| 8,324,914 B2 | 12/2012 | Chen et al. |
| 8,452,546 B1 | 5/2013 | Lathrop |
| 9,057,102 B2 | 6/2015 | Turner et al. |
| 9,121,064 B2 | 9/2015 | Turner et al. |
| 9,127,313 B2 | 9/2015 | Brown et al. |
| 9,546,400 B2 | 1/2017 | Turner et al. |
| 9,556,480 B2 | 1/2017 | Turner et al. |
| 9,678,056 B2 | 6/2017 | Turner et al. |
| 9,738,929 B2 | 8/2017 | Turner et al. |
| 10,131,943 B2 | 11/2018 | Reid et al. |
| 10,689,697 B2 | 6/2020 | Reid et al. |
| 11,085,077 B2 | 8/2021 | Reid et al. |
| 2002/0197618 A1 | 12/2002 | Sampson |
| 2003/0099951 A1 | 5/2003 | Akeson et al. |
| 2005/0159898 A1 | 7/2005 | Yasuda |
| 2005/0272923 A1 | 12/2005 | Zhang et al. |
| 2006/0019259 A1 | 1/2006 | Joyce |
| 2007/0161028 A1 | 7/2007 | Schwartz et al. |
| 2010/0331194 A1 | 12/2010 | Turner et al. |
| 2011/0121840 A1 | 5/2011 | Sanghera et al. |
| 2011/0226623 A1 | 9/2011 | Timp et al. |
| 2013/0023423 A1 | 1/2013 | Kavanagh et al. |
| 2013/0071837 A1 | 3/2013 | Winters-Hilt et al. |
| 2013/0146456 A1 | 6/2013 | Gundlach et al. |
| 2014/0255918 A1 | 9/2014 | Olasagasti et al. |
| 2015/0057948 A1 | 2/2015 | Reid et al. |
| 2015/0152492 A1 | 6/2015 | Brown et al. |
| 2015/0152495 A1 | 6/2015 | Stava et al. |
| 2015/0344944 A1 | 12/2015 | Reid et al. |
| 2016/0162634 A1 | 6/2016 | Reid et al. |
| 2017/0091427 A1 | 3/2017 | Massingham |
| 2017/0096703 A1 | 4/2017 | Dolan et al. |
| 2017/0219557 A1 | 8/2017 | Reid et al. |
| 2017/0233804 A1 | 8/2017 | Reid et al. |
| 2019/0154655 A1 | 5/2019 | Reid et al. |
| 2019/0203286 A1 | 7/2019 | Reid et al. |
| 2019/0310242 A1 | 10/2019 | Reid et al. |

FOREIGN PATENT DOCUMENTS

| | | |
|---|---|---|
| JP | H11-178575 A | 7/1999 |
| JP | 2002-325581 A | 11/2002 |
| JP | 2010-539966 A | 12/2010 |
| JP | 2014-531901 A | 12/2014 |
| WO | WO 2000/028312 A1 | 5/2000 |
| WO | WO 2000/039333 A1 | 7/2000 |
| WO | WO 2000/079257 A1 | 12/2000 |
| WO | WO 2002/042496 A2 | 5/2002 |
| WO | WO 2005/124888 A1 | 12/2005 |
| WO | WO 2006/028508 A2 | 3/2006 |
| WO | WO 2006/100484 A2 | 9/2006 |
| WO | WO 2007/117832 A2 | 10/2007 |
| WO | WO 2007/137225 A2 | 11/2007 |
| WO | WO 2008/092760 A1 | 8/2008 |
| WO | WO 2008/102120 A1 | 8/2008 |
| WO | WO 2008/102121 A1 | 8/2008 |
| WO | WO 2008/124107 A1 | 10/2008 |
| WO | WO 2009/035647 A1 | 3/2009 |
| WO | WO 2009/077734 A2 | 6/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/053820 A1 | 5/2010 |
| WO | WO 2010/086603 A1 | 8/2010 |
| WO | WO 2010/086622 A1 | 8/2010 |
| WO | WO 2010/109197 A2 | 9/2010 |
| WO | WO 2010/117470 A2 | 10/2010 |
| WO | WO 2010/122293 A1 | 10/2010 |
| WO | WO 2011/046706 A1 | 4/2011 |
| WO | WO 2011/067559 A1 | 6/2011 |
| WO | WO 2012/005857 A1 | 1/2012 |
| WO | WO 2012/021149 A1 | 2/2012 |
| WO | WO 2012/033524 A2 | 3/2012 |
| WO | WO 2012/107778 A2 | 8/2012 |
| WO | WO 2012/109483 A2 | 8/2012 |
| WO | WO 2012/135658 A2 | 10/2012 |
| WO | WO 2012/138357 A1 | 10/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/109970 A1 | 7/2013 |
| WO | WO 2013/121224 A1 | 8/2013 |
| WO | WO 2013/123379 A2 | 8/2013 |
| WO | WO 2013/153359 A1 | 10/2013 |
| WO | WO 2013/159042 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A1 | 5/2014 |
| WO | WO 2014/064444 A1 | 5/2014 |
| WO | WO 2014/096830 A1 | 6/2014 |

OTHER PUBLICATIONS

International Preliminary Report on Patentability for Application No. PCT/GB2015/053083, dated Apr. 27, 2017.

Alcock et al., Time-series Similarity Queries Employing a Feature-Based Approach. Proceedings of the 7th Hellenic Conference on Informatics (HCI '99); University of Ioannina, Greece, pp. 1-9, Aug. 26-29, 1999.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Ashkenasy et al., Recognizing a single base in an individual DNA strand: a step toward DNA sequencing in nanopores. Angew Chem Int Ed Engl. Feb. 18, 2005;44(9):1401-4.

Bates et al., Dynamics of DNA molecules in a membrane channel probed by active control techniques. Biophys J. 2003;84(4):2366-2372. doi:10.1016/S0006-3495(03)75042-5.

Batzoglou, Algorithmic challenges in mammalian whole-genome sequence assembly. In: Encyclopedia of genomics, proteomics and bioinformatics. John Wiley and Sons, New York. 2005.

Bell et al., DNA origami nanopores. Nano Lett. Jan. 11, 2012;12(1):512-7. doi: 10.1021/nl204098n. Epub Dec. 29, 2011.

Bokhari et al., A parallel graph decomposition algorithm for DNA sequencing with nanopores. Bioinformatics. Apr. 1, 2005;21(7):889-96. Epub Nov. 11, 2004.

Boufounos et al., Basecalling using hidden Markov models. Journal of the Franklin Institute, vol. 341 :23-36 (2004).

Braha et al., Designed protein pores as components for biosensors. Chem Biol. Jul. 1997;4(7):497-505.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

(56) References Cited

OTHER PUBLICATIONS

Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Chao et al., Constrained sequence alignment. Bull Math Biol. May 1993;55(3):503-24.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Dahl et al., Direct observation of translocation in individual DNA polymerase complexes. J Biol Chem. Apr. 13, 2012;287(16):13407-21. doi:10.1074/jbc.M111.338418. Epub Feb. 29, 2012.
Derrington et al., Nanopore DNA sequencing with MspA. Proc Natl Acad Sci U S A. Sep. 14, 2010;107(37):16060-5. doi: 10.1073/pnas.1001831107.
Devereux et al., A comprehensive set of sequence analysis programs for the VAX. Nucleic Acids Res. Jan. 11, 1984;12(1 Pt 1):387-95.
Edgar, Muscle: multiple sequence alignment with high accuracy and high throughput. Nucleic Acids Res. Mar. 19, 2004;32(5):1792-7. Print 2004.
EP Communication pursuant to Rule 114(2) EPC for Application No. 13706058.8 dated Oct. 19, 2017.
Ervin et al., Simultaneous alternating and direct current readout of protein ion channel blocking events using glass nanopore membranes. Anal Chem. Mar. 15, 2008;80(6):2069-76. doi: 10.1021/ac7021103. Epub Feb. 23, 2008.
Fariselli et al., A new decoding algorithm for hidden Markov models improves the prediction of the topology of all-beta membrane proteins. BMC Bioinformatics. Dec. 1, 2005;6 Suppl 4:S12.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Gordon, Classification. 2nd edition. Chapman and Hall/CRC. 69-109. 1999.
Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.
He et al., Controlling DNA translocation through gate modulation of nanopore wall surface charges. ACS Nano. Jul. 26, 2011;5(7):5509-18. doi: 10.1021/nn201883b. Epub Jun. 17, 2011.
Healy, Nanopore-based single-molecule DNA analysis. Nanomedicine (Lond). Aug. 2007;2(4):459-81.
Hein et al., Statistical alignment: computational properties, homology testing and goodness-of-fit. J Mol Biol. Sep. 8, 2000;302(1):265-79.
Heron et al., Simultaneous measurement of ionic current and fluorescence from single protein pores. J Am Chem Soc. Feb. 11, 2009;131(5):1652-3. doi: 10.1021/ja808128s.
Higgins et al., CLUSTAL: a package for performing multiple sequence alignment on a microcomputer. Gene. Dec. 15, 1988;73(1):237-44.

Ivanov et al., DNA tunneling detector embedded in a nanopore. Nano Lett. Jan. 12, 2011;11(1):279-85. doi: 10.1021/nl103873a. Epub Dec. 6, 2010.
Jain et al., Improved data analysis for the MinION nanopore sequencer. Nat Methods. Apr. 2015; 12(4): 351-356. EPub Feb. 16, 2015. doi: 10.1038/nmeth.3290. Author Manuscript.
Karp et al., Efficient randomized pattern-matching algorithms. IBM J. Res. Development. 1987;31(2):249-260.
Kasianowicz et al., Nanoscopic porous sensors. Annu Rev Anal Chem (Palo Alto Calif). 2008;1:737-66. doi:10.1146/annurev.anchem.1.031207.112818.
Kaxiras et al. Multiscale simulations of complex systems: computation meets reality. Sci Model Simul. 2008; 15:59-65.
Kent WJ. BLAT—the BLAST-like alignment tool. Genome Res. Apr. 2002;12(4):656-64.
Khreich et al., A survey of techniques for incremental learning of HMM parameters. J Info Sciences. Aug. 2012;197:105-130.
Kowalczyk et al., Slowing down DNA translocation through a nanopore in lithium chloride. Nano Lett. Feb. 8, 2012;12(2):1038-44. doi: 10.1021/nl204273h. Epub Jan. 27, 2012.
Lam et al., HMMCONVERTER 1.0: a toolbox for hidden Markov models. Nucleic Acids Res. Nov. 2009;37(21):e139. doi: 10.1093/nar/gkp662.
Lathrop et al., Monitoring the escape of DNA from a nanopore using an alternating current signal. J Am Chem Soc. Feb. 17, 2010;132(6):1878-85. doi:10.1021/ja906951g.
Liang et al., Bayesian Basecalling for DNA Sequence Analysis using Hidden Markov Models. Proceedings of 2006 IEEE Conference on Information Sciences and Systems, CISS, pp. 1599-1604 (2006).
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Loose et al., Real-time selective sequencing using nanopore technology. Nat Methods. Sep. 2016; 13(9): 751-754. EPub Jul. 25, 2016. doi: 10.1038/nmeth.3930.
Luan et al., Base-by-base ratcheting of single stranded DNA through a solid-state nanopore. Phys Rev Lett. Jun. 11, 2010;104(23):238103. Epub Jun. 10, 2010.
Luan et al., Control and reversal of the electrophoretic force on DNA in a charged nanopore. J Phys Condens Matter. Nov. 17, 2010;22(45):454123. doi:10.1088/0953-8984/22/454123. Epub Oct. 29, 2010.
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Mikheyev et al., A first look at the Oxford Nanopore MinION sequencer. Mol Ecol Resour. Nov. 2014;14(6):1097-102. doi: 10.1111/1755-0998.12324. Epub Sep. 24, 2014.
Montal et al., Formation of bimolecular membranes from lipid monolayers and a study of their electrical properties. Proc Natl Acad Sci U S A. Dec. 1972;69(12):3561-6.
Nakane et al. Nanopore sensors for nucleic acid analysis. J. Phys.: Condens. Matter 15 (2003) R1365-R1393.
Olasagasti et al., Replication of individual DNA molecules under electronic control using a protein nanopore. Nat Nanotechnol. Nov. 2010;5(11):798-806. doi: 10.1038/nnano.2010.177. Epub Sep. 26, 2010.
Quinlan et al., C.45: Programs for Machine Learning. Morgan Kaufmann Publishers, ISBN 1-55860-238-0. Ed.:Langley. 1-114. 1993.
Schneider et al., DNA sequencing with nanopores. Nat Biotechnol. Apr. 10, 2012;30(4):326-8. doi: 10.1038/nbt.2181.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Nucleobase recognition in ssDNA at the central constriction of the alpha-hemolysin pore. Nano Lett. Sep. 8, 2010;10(9):3633-7. doi: 10.1021/nl101955a.

(56) References Cited

OTHER PUBLICATIONS

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Suzuki et al., A New Hmnet Construction Algorithm Requiring No Contextual Factors. IEICE. Jun. 1995;E78:662-668.

Takami et al., Automatic Generation of Hidden Markov Networks by a Successive State Splitting Algoritm. IEICE. 1993;J76:2155-2164.

Thompson et al., CLUSTAL W: improving the sensitivity of progressive multiple sequence alignment through sequence weighting, position-specific gap penalties and weight matrix choice. Nucleic Acids Res. Nov. 11, 1994;22(22):4673-80.

Timp et al., DNA base-calling from a nanopore using a Viterbi algorithm. Biophys J. May 16, 2012;102(10):L37-9. doi:10.1016/j.bpj.2012.04.009. Epub May 15, 2012.

United States District Court for the District of Delaware Order. *Pacific Biosciences of California, Inc.* v. *Oxford Nanopore Technologies, Inc.* Civil Action No. 17-275-RGA. Nov. 9, 2017.

United States Patent and Trademark Office. *Oxford Nanopore Technologies Inc.* Petition v *Pacific Biosciences of California, Inc.* for U.S. Pat. No. 9,546,400. Inter Partes Review of claims 1-15. 81 pages. Mar. 15, 2018.

Warren et al., Assembling millions of short DNA sequences using SSAKE. Bioinformatics. Feb. 15, 2007;23(4):500-1. Epub Dec. 8, 2006.

Winters-Hilt et al., A novel, fast, HMM-with-Duration implementation—for application with a new, pattern recognition informed, nanopore detector. BMC Bioinformatics. Nov. 1, 2007;8 Suppl 7:S19.

Winters-Hilt et al., Highly accurate classification of Watson-Crick basepairs on termini of single DNA molecules. Biophys J. Feb. 2003;84(2 Pt 1):967-76.

Winters-Hilt, Machine learning methods for channel current cheminformatics, biophysical analysis, and bioinformatics. University of California Santa Cruz. Mar. 2003. Dissertation. 176 pages.

Zeng et al., PyroHMMvar: a sensitive and accurate method to call short indels and SNPs for Ion Torrent and 454 data. Bioinformatics. Nov. 15, 2013;29(22):2859-68. doi: 10.1093/bioinformatics/btt512. Epub Aug. 31, 2013.

Zerbino et al., Velvet: algorithms for de novo short read assembly using de Bruijn graphs. Genome Res. May 2008;18(5):821-9. doi: 10.1101/gr.074492.107. Epub Mar. 18, 2008.

Zhu et al., Bayesian adaptive sequence alignment algorithms. Bioinformatics. 1998;14(1):25-39.

No Author Listed], Chapter 2: Polymerizer Module from Polymer. 1997. 14 pages. www.esi.umontreal.ca/accelrys/materials/insight400P/polymer/02_Polym.doc.html, Accessed May 17, 2021.

Ainsleigh et al., Hidden Gauss-Markov Models for Signal Classification. IEEE Trans Sig Proc. Jun. 2002;50(6):1355-1367.

Cabello-Aguilar et al., Experimental and simulation studies of unusual current blockade induced by translocation of small oxidized PEG through a single nanopore. Phys Chem Chem Phys. Sep. 7, 2014;16(33):17883-92. doi: 10.1039/c4cp01954g.

Churbanov et al., Duration learning for analysis of nanopore ionic current blockades. BMC Bioinformatics. Nov. 1, 2007;8 Suppl 7(Suppl 7):S14. doi: 10.1186/1471-2105-8-S7-S14.

Fennouri et al., Single molecule detection of glycosaminoglycan hyaluronic acid oligosaccharides and depolymerization enzyme activity using a protein nanopore. ACS Nano. Nov. 27, 2012;6(11):9672-8. doi: 10.1021/nn3031047. Epub Oct. 17, 2012.

Pylkkönen et al., Duration Modeling Techniques for Continuous Speech Recognition. Eighth International Conference on Spoken Language Processing. 2004. 4 pages.

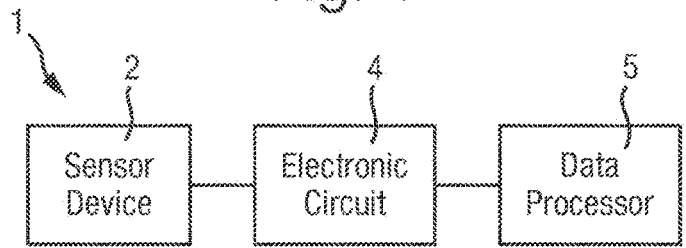
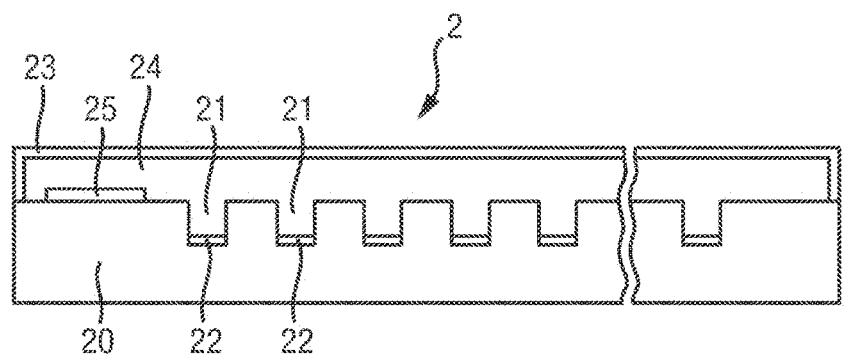

ANALYSIS OF A POLYMER

This Application is a continuation of U.S. application Ser. No. 15/519,325, filed Apr. 14, 2017, which is a national stage filing under 35 U.S.C. § 371 of PCT International Application No. PCT/GB2015/053083, which has an international filing date of Oct. 16, 2015, and claims foreign priority benefits under 35 U.S.C. § 119(a)-(d) or 35 U.S.C. § 365(b) of British application number 1418366.9, filed Oct. 16, 2014, British application number 1418379.2, filed Oct. 16, 2014, and British application number 1507742.3, filed May 6, 2015. The contents of the aforementioned applications are herein incorporated by reference in their entireties.

The first to third aspects of the present invention relate to analysis of a polymer using a biochemical analysis system that comprises at least one sensor element that comprises a nanopore. The fourth aspect of the present invention relates to the estimation of an alignment mapping between a series of measurements of a polymer comprising polymer units, and a reference sequence of polymer units. In all aspects, the polymer may be, for example but without limitation, a polynucleotide in which the polymer units are nucleotides.

There are many types of biochemical analysis system that provide measurements of polymer units for the purpose of determining the sequence. For example but without limitation, one type of measurement system uses a nanopore. Biochemical analysis systems that use a nanopore have been the subject of much recent development. Typically, successive measurements of a polymer are taken from a sensor element comprising a nanopore are taken during translocation of the polymer through the nanopore. Some property of the system depends on the polymer units in the nanopore, and measurements of that property are taken. This type of measurement system using a nanopore has considerable promise, particularly in the field of sequencing a polynucleotide such as DNA or RNA.

Such biochemical analysis systems using nanopores can provide long continuous reads of polymers, for example in the case of polynucleotides ranging from many hundreds to tens of thousands (and potentially more) nucleotides. The data gathered in this way comprises measurements, such as measurements of ion current, where each translocation of the sequence through the sensitive part of the nanopore results in a slight change in the measured property.

Whilst such biochemical analysis systems using nanopores can provide significant advantages, it remains desirable to increase the speed of analysis. The first and second aspects of the present invention are concerned with providing such an increase.

According to a first aspect of the present invention, there is provided a method of controlling a biochemical analysis system for analysing polymers that comprise a sequence of polymer units, wherein the biochemical analysis system comprises at least one sensor element that comprises a nanopore, and the biochemical analysis system is operable to take successive measurements of a polymer from a sensor element, during translocation of the polymer through the nanopore of the sensor element, wherein the method comprises, when a polymer has partially translocated through the nanopore, analysing the series of measurements taken from the polymer during the partial translocation thereof using reference data derived from at least one reference sequence of polymer units to provide a measure of similarity between the sequence of polymer units of the partially translocated polymer and the at least one reference sequence, and responsive to the measure of similarity, operating the biochemical analysis system to reject the polymer and to take measurements from a further polymer.

Such a method involves analysing measurements taken from the polymer when it has partially translocated through the nanopore, i.e. during translocation of the polymer through the nanopore. In particular, the series of measurements taken from the polymer during the partial translocation are analysed using reference data derived from at least one reference sequence of polymer units. This analysis provides a measure of similarity between the sequence of polymer units of the partially translocated polymer and the at least one reference sequence. Responsive to that measure of similarity, action may be taken to reject the polymer to take measurements from a further polymer if the similarity to the reference sequence indicates no further analysis of the polymer is needed, for example because the polymer being measured is not of interest.

The rejection of the polymer allows measurements of a further polymer to be taken without completing the measurement of the polymer initially being measured. This provides a time saving in taking the measurements, because the action is taken "on-the-fly", i.e. during the taking of measurements from a polymer. In typical applications, that time saving may be significant because biochemical analysis systems using nanopores can provide long continuous reads of polymers, whereas the analysis may identify at an early stage in such a read that no further measurements of the polymer currently being measured are needed.

For example in typical applications where the polymer is a polynucleotide, sequencing performed with 100% accuracy would allow an initial determination to be made after measurement of around 30 nucleotides. Thus, taking into account actually achievable accuracies, the determination may be made after measurement of a few hundred nucleotides, typically 250 nucleotides. This compares to the biochemical analysis system being able to perform measurements on sequences ranging in length from many hundreds to tens of thousands (and potentially more) nucleotides.

The method potentially provides a significantly faster time to result wherein continued measurement is carried out only on those polymers determined to be of interest and those determined to be not of interest are rejected. This advantage of reducing the amount of wasted data acquisition is particularly significant in applications where a large amount of data acquisition is required. The resultant time saving is useful in itself or might be used for example to obtain a greater coverage and therefore a higher sequencing accuracy than might otherwise be obtained with the time and resources available.

The analysis that provides a measure of similarity between the sequence of polymer units of the partially translocated polymer and the at least one reference sequence may in itself use known techniques for comparing measurements to references. However, in contrast to the present method, such known techniques are typically performed measurements taken after the translocation has been completed.

The method may be applied to a wide range of applications. Depending on the application, the measure of similarity may indicate similarity with the entirety of the reference sequence, or with a portion of the reference sequence.

According to a second aspect of the present invention, there is provided a method of controlling a biochemical analysis system for analysing polymers that comprise a sequence of polymer units, wherein the biochemical analysis system comprises at least one sensor element that comprises a nanopore, and the biochemical analysis system is operable to take successive measurements of a polymer from a sensor element, during translocation of the polymer through the nanopore of the sensor element, wherein the method comprises, when a polymer has partially translocated through the nanopore, analysing the series of measurements taken from the polymer during the partial translocation thereof by deriving a measure of fit to a model that treats the measurements as observations of a series of k-mer states of different possible types and comprises: transition weightings, in respect of each transition between successive k-mer states in the series of k-mer states, for possible transitions between the possible types of k-mer state; and emission weightings, in respect of each type of k-mer state that represent the chances of observing given values of measurements for that k-mer, and responsive to the measure of fit, operating the biochemical analysis system to reject the polymer and to take measurements from a further polymer.

Such a method involves analysing measurements taken from the polymer when it has partially translocated through the nanopore, i.e. during translocation of the polymer through the nanopore. In particular, the series of measurements taken from the polymer during the partial translocation are analysed using reference data derived from at least one reference sequence of polymer units. This analysis provides a measure of fit to a model. Responsive to that measure of fit, action may be taken to reject the polymer and to take measurements from a further polymer, if the measure of fit indicates measurements are of poor quality as determined by the model such that further translocation and measurement is not warranted.

The rejection of the polymer allows measurements of a further polymer to be taken without completing the measurement of the polymer initially being measured. This provides a time saving in taking the measurements, because the action is taken "on-the-fly", i.e. during the taking of measurements from a polymer. In typical applications, that time saving may be significant because biochemical analysis systems using nanopores can provide long continuous reads of polymers, whereas the analysis may identify at an early stage that the measurements are of poor quality.

The first and second aspects of the present invention are the same except for the basis on which the biochemical analysis system is operated to reject the polymer and to take measurements from a further polymer. Thus, the optional features in accordance with the first aspect of the invention set out in dependent claims 2 to 20 may be applied mutatis mutandis to the second aspect of the invention. Also, all the following features of the method apply equally to methods in accordance with either the first or second aspect of the invention.

The rejection of the polymer may occur in different ways.

In a first approach, the at least one sensor element is operable to eject a polymer that is translocating through the nanopore. In that case, the step of operating the biochemical analysis system to reject the polymer and to take measurements from a further polymer may be performed by operating the sensor element to eject the polymer from the nanopore and accept a further polymer in the nanopore.

In a second approach, the biochemical analysis system comprises an array of sensor elements and is operable to take successive measurements of a polymer from sensor elements selected in a multiplexed manner. In that case, the step of operating the biochemical analysis system to reject the polymer and to take measurements from a further polymer may comprise operating the biochemical analysis system to cease taking measurements from the currently selected sensor element and to start taking measurements from a newly selected sensor element.

These two approaches may be used in combination.

The third aspect of the present invention is concerned with an application of a specific form of biochemical analysis that may be performed using nanopores.

According to a third aspect of the present invention, there is provided a method of sorting polymers that each comprise a sequence of polymer units, the method using a system that comprises a sample chamber containing a sample comprising the polymers, a collection chambers sealed from the sample chamber and a sensor element comprising a nanopore that communicates between the sample chamber and the collection chamber, the method comprising causing successive polymers from the sample chamber to start translocation through the nanopore, and, during the translocation of each polymer:

taking successive measurements of the polymer from the sensor element;

analysing the series of measurements taken from the polymer during the partial translocation thereof using reference data derived from at least one reference sequence of polymer units to provide a measure of similarity between the sequence of polymer units of the partially translocated polymer and the at least one reference sequence, in dependence on the measure of similarity, selectively completing the translocation of the polymer into the collection chamber or else ejecting the polymer back into the sample chamber.

Thus, the method makes use of the measure of similarity provided by the analysis of the series of measurements taken from the polymer during the partial translocation. The analysis may in itself use known techniques for comparing measurements to references. However, the measure of similarity is used to determine whether the polymer is to be collected. If so, then the translocation of the polymer into the collection chamber is completed. Otherwise, the polymer is ejected back into the sample chamber. In this way, the selected polymers are collected in the collection chamber. The collected polymers may be recovered, for example after completing translocation of polymers from the sample, or alternatively during translocation of polymers from the sample, for example by providing the system with a fluidics system that is suitable for that.

The method may be applied to a wide range of applications. For example, the method could be applied to polymers that are polynucleotides, for example viral genomes or plasmids. A viral genome typically has a length of order 10-15 kB (kilobases) and a plasmid typically has a length of order 4 kB. In such examples, the polynucleotides would not have to be fragmented and could be collected whole. The collected viral genome or plasmid could be used in any way, for example to transfect a cell.

The reference sequence of polymer units from which the reference data is derived could be a wanted sequence. In that case, the step of selectively completing the translocation of the polymer into the collection chamber is performed responsive to the measure of similarity indicating that the partially translocated polymer is the wanted sequence. However, this is not essential. In some applications, the reference sequence of polymer units from which the reference data is derived could be an unwanted sequence. In that case, the step of selectively completing the translocation of the polymer into the collection chamber is performed responsive to the measure of similarity indicating that the partially translocated polymer is not the unwanted sequence.

Depending on the application, the measure of similarity may indicate similarity with the entirety of the reference sequence, or with a portion of the reference sequence.

The system may comprise plural collection chambers and, in respect of each collection chamber, a sensor element comprising a nanopore that provides communication between the sample chamber and the respective collection chamber. This allows the method being performed in respect of plural nanopores in parallel. As well as providing the capability of speeding up the sorting method, that may allow collection of different polymers in different collection chambers. To achieve that, the reference data and criteria for collection are selected accordingly. In one example, the method may be performed using different reference data in respect of different nanopores. In another example, the method may be performed using the same reference data in respect of different nanopores, but said step of selectively completing the translocation of the polymer into the collection chamber is performed with different dependence on the measure of similarity in respect of different nanopores.

According to further aspects of the present invention, there are provided biochemical analysis systems that implement a method similar to that of the first, second or third aspect of the invention.

The fourth aspect of the present invention is concerned with alignment between a series of measurements of a polymer comprising polymer units, and a reference sequence of polymer units.

Some types of measurement system take measurements of polymers that are dependent on a k-mer, being k polymer units of the polymer, where k is an integer, By way of definition, a group of k polymer units is hereinafter referred to as a k-mer. In general, k can take the value one, in which case a k-mer is a single polymer unit or can be a plural integer. Each given polymer unit may be of different types, depending on the nature of the polymer. For example, in the case that the polymer is a polynucleotide, the polymer units are nucleotides and the different types are nucleotides including different nucleobases (such as cytosine, guanine, etc.). Each given k-mer may therefore also be of different types, corresponding to different combinations of the different types of each polymer unit of the k-mer.

As to the estimation of the polymer units from the measurements, in practical types of the measurement system, it is difficult to provide measurements that are dependent on a single polymer unit. Instead the value of each measurement is dependent on a k-mer, where k is a plural integer. Conceptually, this might be thought of as the measurement system having a "blunt reader head" that is bigger than the polymer unit being measured. In such a situation, the number of different k-mers to be resolved increases to the power of k. When measurements are dependent on large numbers of polymer units (large values of k), measurements taken from k-mers of different types can be difficult to resolve, because they provide signal distributions that overlap, especially when noise and/or artefacts in the measurement system are considered. This is to the detriment of estimating the underlying sequence of polymer units.

Where k is a plural integer, it is possible to combine information from multiple measurements of overlapping k-mers that each depend in part on the same polymer unit to obtain a single value that is resolved at the level of a polymer unit. By way of example, WO-2013/041878 discloses a method of estimating a sequence of polymer units in a polymer from at least one series of measurements related to the polymer that makes use of a model in respect of the series of measurements that treats the measurements as observations of a series of k-mer states of different possible types. The model comprises: transition weightings, in respect of each transition between successive k-mer states in the series of k-mer states, for possible transitions between the possible types of k-mer state; and emission weightings, in respect of each type of k-mer state that represent the chances of observing given values of measurements for that k-mer. The model may be for example a Hidden Markov Model (HMM). Such a model can improve the accuracy of the estimation by taking plural measurements into account in the consideration of the likelihood predicted by the model of the series of measurements being produced by sequences of polymer units.

In many circumstances, it is desirable to estimate an alignment mapping between a series of measurements of a polymer comprising polymer units, and a reference sequence of polymer units. Such estimation of an alignment mapping may be used in a variety of applications such as comparison to a reference to provide identification or detection of the presence, absence or extent of a polymer in a sample, for example to provide a diagnosis. The potential range of specific applications is vast and could be applied to the detection of any analyte having a DNA sequence.

Existing techniques involve initially estimating the sequence of polymer units that has been measured and then estimating an alignment mapping to the reference sequence of polymer units by comparing the identity of the polymer units. Many fast alignment algorithms have been developed for application to the case that the polymer units are nucleotides (often referred to in the literature as bases). Examples of fast alignment algorithms are BLAST (Basic Local Alignment Search Tool), FASTA and HMMER, and derivatives thereof. Fast alignment algorithms typically look for highly similar smaller regions which is a relatively quick process, and then extend out to less similar larger regions which is a slower process. Such algorithms have been applied in situations where they indicate the identity of the polymer unit by providing a similarity score on whether the polymer being measured matches a reference in a minimal time frame. In these types of technique the identity of the polymer units in the estimated sequence and in the reference is compared directly. When referring to polymer units that are bases, the techniques may be referred to as involving a comparison in "base-space", in contrast to a comparison between measurements which would be in "measurement space".

However, such techniques have limited accuracy in estimation of the alignment mapping, or in other words a limited discriminatory power. This is because the initial step of estimating the sequence of polymer units inherently causes loss of information about the identity of the polymer units that is present in the measurements themselves.

It would be desirable to provide a method of estimating an alignment mapping that provides increased accuracy as compared to such existing techniques.

According to the fourth aspect of the present invention, there is provided a method of estimating an alignment mapping between (a) a series of measurements of a polymer comprising polymer units, wherein the measurements are dependent on a k-mer, being k polymer units of the polymer, where k is an integer, and (b) a reference sequence of polymer units;

the method using a reference model that treats the measurements as observations of a reference series of k-mer states corresponding to the reference sequence of polymer units, wherein the reference model comprises:

transition weightings for transitions between the k-mer states in the reference series of k-mer states; and in respect of each k-mer state, emission weightings for different measurements being observed when the k-mer state is observed; and the method comprising applying the reference model to the series of measurements to derive an estimate of an alignment mapping between the series of measurements and the reference series of k-mer states corresponding to the reference sequence of polymer units.

This method therefore uses a reference model in respect of the reference sequence. The reference model treats the measurements as observations of a reference series of k-mer states corresponding to the reference sequence of polymer units, and comprises transition weightings for transitions between the k-mer states in the reference series of k-mer states; and in respect of each k-mer state, emission weightings for different measurements being observed when the k-mer state is observed. The may be, for example but without limitation a HMM. As a result, the method can improve the accuracy of the estimation of the alignment method, compared to the known techniques discussed above that involve initially estimating the sequence of polymer units and then estimating an alignment mapping to the reference sequence of polymer units by comparing the identity of the polymer units. This is for the following reasons.

In general terms, the use of the reference model is similar to the model disclosed in WO-2013/041878 to estimate the sequence of polymer units, for example using transition weightings and emission weightings of a similar form, and applying the same mathematical treatment to the model. However, the reference model itself is different from the model disclosed in WO-2013/041878 which is a generic model of the measurement system, wherein each k-mer state may in general be of any of the possible types of k-mer state. Thus, transition weightings are provided in respect of each transition between successive k-mer states in the series of k-mer states, for various possible transitions between the possible types of the k-mer states. In contrast the reference model used in the present method is a model of a reference series of k-mer states corresponding to the reference sequence of polymer units. Thus, transition weightings are provided for transitions between the k-mer states in the reference series of k-mer states.

This similarity means that the method of the present invention can utilise the power of the model disclosed in WO-2013/041878. Information about the identity of the polymer units that is present in the measurements that is dependent on overlapping k-mers is used to inform the result. Due to the different nature of the reference model itself, application of the reference model can provide an alignment mapping between the series of measurements and the reference series of k-mer states corresponding to the reference sequence of polymer units, and hence the alignment mapping between the series of measurements and the reference sequence of polymer units.

In some implementations, the derived estimate of the alignment mapping may comprise, for each measurement in the series, a discrete estimate of a mapped k-mer state in the reference series of k-mer states. As an example where the model is an HMM, this may be achieved by use of the Viterbi algorithm to derive the estimate of the alignment mapping.

In other implementations, the derived estimate of the alignment mapping may comprise, for each measurement in the series, weightings in respect of different mapped k-mer states in the reference series of k-mer states. As an example where the model is an HMM, this may be achieved by use of the Forwards-Backwards algorithm to derive the estimate of the alignment mapping.

Optionally, the method may further comprise deriving a score representing the likelihood that the estimate of the alignment mapping is correct. This score provides a measure of the similarity the polymer being measured and the reference sequence of polymer units. This is useful in a wide range of applications by providing information on the identity of the polymer being measured as compared to a reference sequence.

In some cases, this score may be derived directly from the application of the model. An example of this is where the model is an HMM and the Viterbi algorithm is applied.

In other cases where the derived estimate of the alignment mapping may comprise, for each measurement in the series, weightings in respect of different mapped k-mer states in the reference series of k-mer states, this score may be derived from those weightings themselves.

The source of the reference model may vary depending on the application.

In some applications, the reference model may be pre-stored having been generated previously from the reference sequence of polymer units or from measurements taken from the reference sequence of polymer units.

In other applications, the reference model may be generated at the time the method is performed, for example as follows.

In a first example, the reference model may be generated from the reference sequence of polymer units. This is useful in applications where the reference sequence is known, for example from a library or from earlier experiments.

In this case, generation of the reference model may be performed using stored emission weightings in respect of a set of possible types of k-mer state. Advantageously, this allows generation of the reference model for any reference sequence of polymer units, based solely on the stored data concerning the emission weightings for the possible types of k-mer state.

For example, the reference model may be generated by a process comprising: deriving the series of k-mer states corresponding to received reference sequence of polymer units; and generating the reference model by generating the transition weightings for transitions between the k-mer states in the derived series of k-mer states, and by selecting emission weightings for each k-mer state in the derived series from the stored emission weightings according to the type of the k-mer state.

In a second example, the reference model may be generated from a series of reference measurements of a polymer that comprises the reference sequence of polymer units. This is useful, for example, in applications where the reference sequence of polymer units is measured contemporaneously with the target polymer. In particular, in this example there is no requirement that the identity of the polymer units in the reference sequence are themselves known.

For example, the reference model may be generated by a process using a further model that treats the series of reference measurements as observations of a further series of k-mer states of different possible types, wherein the further model comprises: in respect of each transition between successive k-mer states in the further series of k-mer states, transition weightings for possible transitions between the possible types of the k-mer states; and in respect of each type of k-mer state, emission weightings for different measurements being observed when the k-mer state is of that type. Such a further model may of itself be a model of the type disclosed in WO-2013/041878. In this case the reference model may be generated by a process comprising: generating the reference series of estimates of k-mer states by applying the further model to the series of reference measurements; and generating the reference model by generating transition weightings for transitions between the k-mer states in the generated reference series of estimates of k-mer states and by selecting emission weightings for each k-mer state in the generated reference series of estimates from the weightings of the further model according to the type of the k-mer state.

Generation of the model may be part of a larger framework of model training examining a large collection of reference measurements derived from observing a large collection of series of k-mer states in order to find the unknown parameters of a mathematical model, such as the emission and transition weightings. Typically the expectation-maximisation (EM) algorithm can be used to find maximum likelihood estimates when the model contains latent (hidden) variables. In the specific case of HMMs the Baum-Welch algorithm may be used. Such algorithms are iterative: initial guesses are made for the parameters of the model, with updates being applied by examining a set of training measurements. Application of the resultant HMM to a second distinct set of measurements will yield improved results (assuming the second set can be described by the same model as the training data).

According to further aspects of the present invention, there is provided a computer program capable of implementing a method according to the fourth aspect of the invention, or an analysis system that implements a method according to the fourth aspect of the invention.

To allow better understanding, embodiments of the present invention will now be described by way of non-limitative example with reference to the accompanying drawings, in which:

FIG. 1 is a schematic diagram of a biochemical analysis system;

FIG. 2 is a cross-sectional view of the sensor device of the system;

Figure 3:
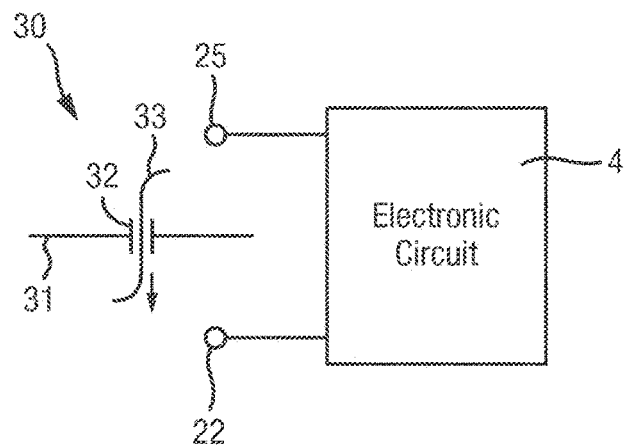
FIG. 3 is a schematic view of a sensor element of the sensor device.

A number of nucleotide and amino acid sequences may be of use in the described embodiments. In particular:

SEQ ID NO: 1 is the nucleotide sequence encoding the pore MS-(B1)8 (=MS-(D90N/D91N/D93N/D118R/D134R/E139K)8);

SEQ ID NO: 2 is the amino acid sequence encoding the pore MS-(B1)8 (=MS-(D90N/D91N/D93N/D118R/D134R/E139K)8);

SEQ ID NO: 3 is the nucleotide sequence encoding the pore MS-(B2)8 (=MS-(L88N/D90N/D91N/D93N/D118R/D134R/E139K)8);

SEQ ID NO: 4 is the amino acid sequence encoding the pore MS-(B2)8 (=MS-(L88N/D90N/D91N/D93N/D118R/D134R/E139K)8). The amino acid sequence of B2 is identical to that of B1 except for the mutation L88N;

SEQ ID NO: 5 is the sequence for wild type $E.$ $coli$ Exonuclease I (WT EcoExo I), a preferred polynucleotide handling enzyme;

SEQ ID NO: 6 is the sequence for $E.$ $coli$ Exonuclease III, a preferred polynucleotide handling enzyme;

SEQ ID NO: 7 is the sequence for $T.$ $thermophilus$ RecJ, a preferred polynucleotide handling enzyme;

SEQ ID NO: 8 is the sequence for bacteriophage lambda exonuclease, a preferred polynucleotide handling enzyme; and SEQ ID NO: 9 is the sequence for Phi29 DNA polymerase, a preferred polynucleotide handling enzyme.

The various features described below are examples and not limitative. Also, the features described are not necessarily applied together and may be applied in any combination.

There will first be described the nature of the polymer to which the present invention may be applied.

The polymer comprises a sequence of polymer units. Each given polymer unit may be of different types (or identities), depending on the nature of the polymer.

The polymer may be a polynucleotide (or nucleic acid), a polypeptide such as a protein, a polysaccharide, or any other polymer. The polymer may be natural or synthetic. The polymer units may be nucleotides. The nucleotides may be of different types that include different nucleobases.

The polynucleotide may be deoxyribonucleic acid (DNA), ribonucleic acid (RNA), cDNA or a synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The polynucleotide may be single-stranded, be double-stranded or comprise both single-stranded and double-stranded regions. Typically cDNA, RNA, GNA, TNA or LNA are single stranded.

The nucleotide may be of any type. The nucleotide can be naturally occurring or artificial. A nucleotide typically contains a nucleobase (which may be shortened herein to "base"), a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

The nucleotide can include a damaged or epigenetic base. The nucleotide can be labelled or modified to act as a marker with a distinct signal. This technique can be used to identify the absence of a base, for example, an abasic unit or spacer in the polynucleotide.

Of particular use when considering measurements of modified or damaged DNA (or similar systems) are the methods where complementary data are considered. The additional information provided allows distinction between a larger number of underlying states.

The polymer may also be a type of polymer other than a polynucleotide, some non-limitative examples of which are as follows.

The polymer may be a polypeptide, in which case the polymer units may be amino acids that are naturally occurring or synthetic.

The polymer may be a polysaccharide, in which case the polymer units may be monosaccharides.

Particularly where the biochemical analysis system 1 comprises a nanopore and the polymer comprises a polynucleotide, the polynucleotide may be long, for example at least 5 kB (kilo-bases), i.e. at least 5,000 nucleotides, or at least 30 kB (kilo-bases), i.e. at least 30,000 nucleotides.

Herein, the term 'k-mer' refers to a group of k-polymer units, where k is a positive integer, including the case that k is one, in which the k-mer is a single polymer unit. In some contexts, reference is made to k-mers where k is a plural integer, being a subset of k-mers in general excluding the case that k is one.

Each given k-mer may therefore also be of different types, corresponding to different combinations of the different types of each polymer unit of the k-mer.

FIG. 1 illustrates a biochemical analysis system 1 for analysing polymers, that may also be used for sorting polymers. Reverting to FIG. 1, the biochemical analysis system 1 comprises a sensor device 2 connected to an electronic circuit 4 which is in turn connected to a data processor 6.

There will first be described some examples in which the sensor device 2 comprises an array of sensor elements that each comprise a biological nanopore.

In a first form, the sensor device 2 may have a construction as shown in cross-section in FIG. 2 comprising a body 20 in which there is formed an array of wells 21 each being a recess having a sensor electrode 22 arranged therein. A large number of wells 21 is provided to optimise the data collection rate of the system 1. In general, there may be any number of wells 21, typically 256 or 1024, although only a few of the wells 21 are shown in FIG. 2. The body 20 is covered by a cover 23 that extends over the body 20 and is hollow to define a sample chamber 24 into which each of the wells 21 opens. A common electrode 25 is disposed within the sample chamber 24. In this first form, the sensor device 2 may be an apparatus as described in further detail in WO-2009/077734, the teachings of which may be applied to the biochemical analysis system 1, and which is incorporated herein by reference.

In a second form, the sensor device 2 may have a construction as described in detail in WO-2014/064443, the teachings of which may be applied to the biochemical analysis system 1, and which is incorporated herein by reference. In this second form, the sensor device 2 has a generally similar configuration to the first form, including an array of compartments which are generally similar to the wells 21 although they have a more complicated construction and which each contain a sensor electrode 22.

In order to facilitate collection of samples from the collection chambers, the sensor device may be configured such that the collection chambers 21 are detachable from the underlying respective electrodes 22 in order to expose the sample contained therein. Such a device configuration is described in more detail in GB patent application no. 1418512.8.

The sensor device 2 is prepared to form an array of sensor elements 30, one of which is shown schematically in FIG. 3. Each sensor element 30 is made by forming a membrane 31 across a respective well 21 in the first form of the sensor device 2 or across each compartment in the second form of the sensor device 2, and then by inserting a pore 32 into the membrane 31. The membrane 31 seals the respective well 21 from the sample chamber 24. The membrane 31 may be made of amphiphilic molecules such as lipid.

The pore 32 is a biological nanopore. The pore 32 communicates between the sample chamber 24 and the well 21, in a known manner.

This preparation may be performed for the first form of the sensor device 2 using the techniques and materials described in detail in WO-2009/077734, or for the second form of the sensor device 2 using the techniques and materials described in detail in WO-2014/064443.

Each sensor element 30 is capable of being operated to take electrical measurements from a polymer during translocation of the polymer 33 through the pore 32, using the sensor electrode 22 in respect of each sensor element 30 and the common electrode 25. The translocation of the polymer 33 through the pore 32 generates a characteristic signal in the measured property that may be observed, and may be referred to overall as an "event".

In this example, the pore 32 is a biological pore, which may have the following properties.

The biological pore may be a transmembrane protein pore. Transmembrane protein pores for use in the methods described herein can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

A suitable transmembrane protein pore may be derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. The pore may also comprise one or more constructs that comprise two or more covalently attached monomers derived from Msp. Suitable pores are disclosed in WO-2012/107778. The pore may be derived from MspA or a homolog or paralog thereof.

The biological pore may be a naturally occurring pore or may be a mutant pore. Typical pores are described in WO-2010/109197, Stoddart D et al., Proc Natl Acad Sci, 12; 106(19):7702-7, Stoddart D et al., Angew Chem Int Ed Engl. 2010; 49(3):556-9, Stoddart D et al., Nano Lett. 2010 Sep. 8; 10(9):3633-7, Butler T Z et al., Proc Natl Acad Sci 2008; 105(52):20647-52, and WO-2012/107778.

The biological pore may be MS-(B1)8. The nucleotide sequence encoding B1 and the amino acid sequence of B1 are Seq ID: 1 and Seq ID: 2.

The biological pore is more preferably MS-(B2)8. The amino acid sequence of B2 is identical to that of B1 except for the mutation L88N. The nucleotide sequence encoding B2 and the amino acid sequence of B2 are Seq ID: 3 and Seq ID: 4.

The biological pore may be inserted into a membrane, such as an amphiphilic layer, for example a lipid bilayer. An amphiphilic layer is a layer formed from amphiphilic molecules, such as phospholipids, which have both hydrophilic and lipophilic properties. The amphiphilic layer may be a monolayer or a bilayer. The amphiphilic layer may be a co-block polymer such as disclosed by (Gonzalez-Perez et al., Langmuir, 2009, 25, 10447-10450) or by PCT/GB2013/052767, published as WO2014/064444. Alternatively, a biological pore may be inserted into a solid state layer.

The pore 32 is an example of a nanopore. More generally, the sensor device 2 may have any form comprising at least one sensor element 30 that is capable of being operated to take measurements from a polymer during translocation of the polymer through a nanopore.

A nanopore is a pore, typically having a size of the order of nanometres, that allows the passage of polymers therethrough. A property that depends on the polymer units translocating through the pore may be measured. The property may be associated with an interaction between the polymer and the nanopore. Interaction of the polymer may occur at a constricted region of the nanopore. The biochemical analysis system 1 measures the property, producing a measurement that is dependent on the polymer units of the polymer.

Alternatively, the nanopore may be a solid state pore comprising an aperture formed in a solid state layer. In that case, it may have the following properties.

Such a solid state layer is typically not of biological origin. In other words, a solid state layer is typically not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO-2009/035647 and WO-2011/046706.

When the solid state pore is an aperture in a solid state layer, the aperture may be modified, chemically, or otherwise, to enhance its properties as a nanopore.

A solid state pore may be used in combination with additional components which provide an alternative or additional measurement of the polymer such as tunneling electrodes (Ivanov A P et al., Nano Lett. 2011 Jan. 12; 11(1): 279-85), or a field effect transistor (FET) device (WO-2005/124888). Suitable solid state pores may be formed by known processes including for example those described in WO-00/79257.

In the example of the biochemical analysis system 1 shown in FIG. 1, the measurements are electrical measurements, in particular current measurements of the ion current flowing through the pore 32. In general, these and other electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and WO-2000/28312. Alternatively, electrical measurements may be made using a multi-channel system, for example as described in WO-2009/077734 and WO-2011/067559.

In order to allow measurements to be taken as the polymer translocates through the pore 32, the rate of translocation can be controlled by a polymer binding moiety. Typically the moiety can move the polymer through the pore 32 with or against an applied field. The moiety can be a molecular motor using for example, in the case where the moiety is an enzyme, enzymatic activity, or as a molecular brake. Where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, moieties that interact with that polymer type can be used. The polymer interacting moiety may be any disclosed in WO-2010/086603, WO-2012/107778, and Lieberman K R et al, J Am Chem Soc. 2010; 132(50):17961-72), and for voltage gated schemes (Luan B et al., Phys Rev Lett. 2010; 104(23):238103).

A polymer binding moiety can be used in a number of ways to control the polymer motion. The moiety can move the polymer through the pore 32 with or against the applied field. The moiety can be used as a molecular motor using for example, in the case where the moiety is an enzyme, enzymatic activity, or as a molecular brake. The translocation of the polymer may be controlled by a molecular ratchet that controls the movement of the polymer through the pore. The molecular ratchet may be a polymer binding protein.

For polynucleotides, the polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme may be derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in WO-2010/086603.

Preferred enzymes are polymerases, exonucleases, helicases and topoisomerases, such as gyrases. Suitable enzymes include, but are not limited to, exonuclease I from *E. coli* (Seq ID: 5), exonuclease III enzyme from *E. coli* (Seq ID: 6), RecJ from *T. thermophilus* (Seq ID: 7) and bacteriophage lambda exonuclease (Seq ID: 8) and variants thereof. Three subunits comprising the sequence shown in Seq ID: 8 or a variant thereof interact to form a trimer exonuclease. The enzyme is preferably derived from a Phi29 DNA polymerase. An enzyme derived from Phi29 polymerase comprises the sequence shown in Seq ID: 9 or a variant thereof.

A variant of Seq IDs: 5, 6, 7, 8 or 9 is an enzyme that has an amino acid sequence which varies from that of Seq IDs: 5, 6, 7, 8 or 9 and which retains polynucleotide binding ability. The variant may include modifications that facilitate binding of the polynucleotide and/or facilitate its activity at high salt concentrations and/or room temperature.

Over the entire length of the amino acid sequence of Seq IDs: 5, 6, 7, 8 or 9, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of Seq IDs: 5, 6, 7, 8 or 9 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed above with reference to Seq ID: 2. The enzyme may be covalently attached to the pore as discussed above.

Suitable strategies for single strand DNA sequencing are the translocation of the DNA through the pore 32, both cis to trans and trans to cis, either with or against an applied potential. The most advantageous mechanism for strand sequencing is the controlled translocation of single strand DNA through the pore 32 under an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential. Alternatively, the single strand DNA dependent polymerases can act as molecular brake slowing down the movement of a polynucleotide through the pore. Any moieties, techniques or enzymes described in WO-2012/107778 or WO-2012/033524 could be used to control polymer motion.

In general, when the measurement is current measurement of ion current flow through the pore 32, the ion current may typically be the DC ion current, although in principle an alternative is to use the AC current flow (i.e. the magnitude of the AC current flowing under application of an AC voltage).

The biochemical analysis system 1 may take electrical measurements of types other than current measurements of ion current through a nanopore as described above.

Other possible electrical measurement include: current measurements, impedance measurements, tunneling measurements (for example as disclosed in Ivanov A P et al., Nano Lett. 2011 Jan. 12; 11(1):279-85), and field effect transistor (FET) measurements (for example as disclosed in WO2005/124888).

As an alternative to electrical measurements, the biochemical analysis system 1 may take optical measurements. A suitable optical method involving the measurement of fluorescence is disclosed by J. Am. Chem. Soc. 2009, 131 1652-1653.

The measurement system 8 may take electrical measurements of types other than current measurements of ion current through a nanopore as described above. Possible electrical measurement include: current measurements, impedance measurements, tunneling measurements (for example as disclosed in Ivanov A P et al., Nano Lett. 2011 Jan. 12; 11(1):279-85), and field effect transistor (FET) measurements (for example as disclosed in WO2005/124888).

Optical measurements may be combined with electrical measurements (Soni G V et al., Rev Sci Instrum. 2010 January; 81(1):014301).

The biochemical analysis system 1 may take simultaneous measurements of different natures. The measurement may be of different natures because they are measurements of different physical properties, which may be any of those described above. Alternatively, the measurements may be of different natures because they are measurements of the same physical properties but under different conditions, for example electrical measurements such as current measurements under different bias voltages.

Figure 4:
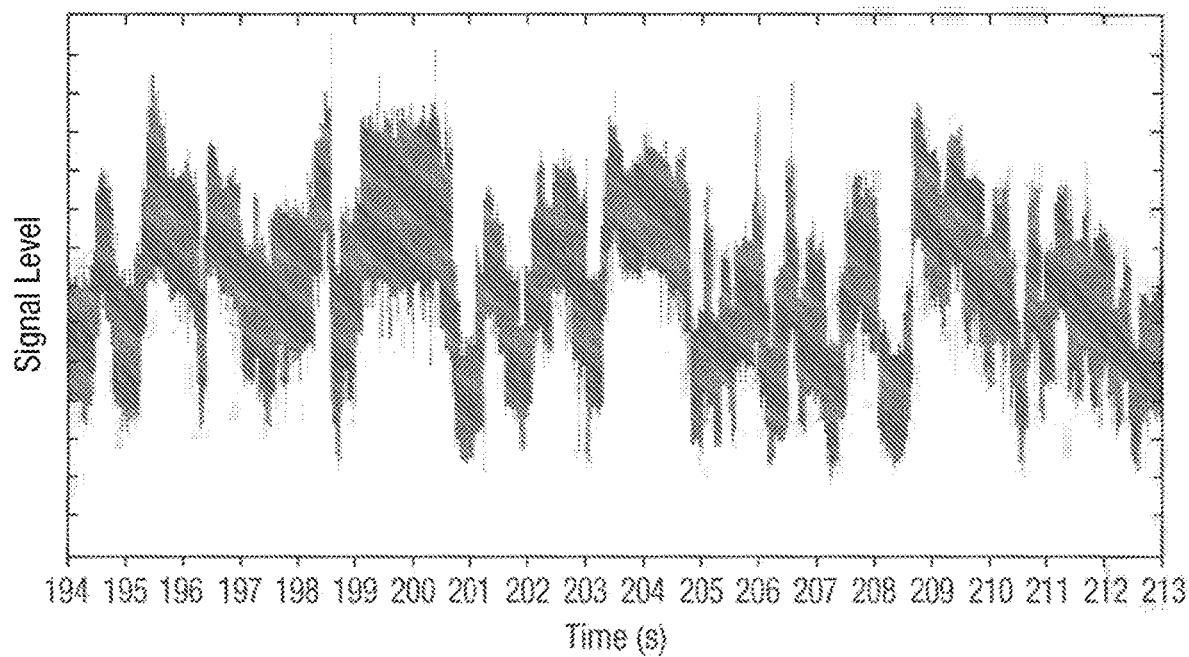
FIG. 4 is a plot of a signal of an event measured over time by a measurement system.

A typical form of the signal output by many types of the sensor device 2 as a series of raw measurements 11 is a "noisy step wave", although without limitation to this signal type. An example of a series of raw measurements 11 having this form is shown in FIG. 4 for the case of an ion current measurement obtained using a type of the measurement system 8 comprising a nanopore.

Typically, each measurement taken by the biochemical analysis system 1 is dependent on a k-mer, being k polymer units of the respective sequence of polymer units, where k is a positive integer. Although ideally the measurements would be dependent on a single polymer unit (i.e. where k is one), with many typical types of the biochemical analysis system 1, each measurement is dependent on a k-mer of plural polymer units (i.e. where k is a plural integer). That is, each measurement is dependent on the sequence of each of the polymer units in the k-mer where k is a plural integer.

In a series of measurements taken by the biochemical analysis system 1, successive groups of plural measurements are dependent on the same k-mer. The plural measurements in each group are of a constant value, subject to some variance discussed below, and therefore form a "level" in a series of raw measurements. Such a level may typically be formed by the measurements being dependent on the same k-mer (or successive k-mers of the same type) and hence correspond to a common state of the biochemical analysis system 1.

The signal moves between a set of levels, which may be a large set. Given the sampling rate of the instrumentation and the noise on the signal, the transitions between levels can be considered instantaneous, thus the signal can be approximated by an idealised step trace.

The measurements corresponding to each state are constant over the time scale of the event, but for most types of the biochemical analysis system 1 will be subject to variance over a short time scale. Variance can result from measurement noise, for example arising from the electrical circuits and signal processing, notably from the amplifier in the particular case of electrophysiology. Such measurement noise is inevitable due the small magnitude of the properties being measured. Variance can also result from inherent variation or spread in the underlying physical or biological system of the biochemical analysis system 1. Most types of the biochemical analysis system 1 will experience such inherent variation to greater or lesser extents. For any given types of the biochemical analysis system 1, both sources of variation may contribute or one of these noise sources may be dominant.

In addition, typically there is no a priori knowledge of number of measurements in the group, this varying unpredictably.

These two factors of variance and lack of knowledge of the number of measurements can make it hard to distinguish some of the groups, for example where the group is short and/or the levels of the measurements of two successive groups are close to one another.

The series of raw measurements may take this form as a result of the physical or biological processes occurring in the biochemical analysis system 1. Thus, in some contexts each group of measurements may be referred to as a "state".

For example, in some types of the biochemical analysis system 1, the event consisting of translocation of the polymer through the pore 32 may occur in a ratcheted manner. During each step of the ratcheted movement, the ion current flowing through the nanopore at a given voltage across the pore 32 is constant, subject to the variance discussed above. Thus, each group of measurements is associated with a step of the ratcheted movement. Each step corresponds to a state in which the polymer is in a respective position relative to the pore 32. Although there may be some variation in the precise position during the period of a state, there are large scale movements of the polymer between states. Depending on the nature of the biochemical analysis system 1, the states may occur as a result of a binding event in the nanopore.

The duration of individual states may be dependent upon a number of factors, such as the potential applied across the pore, the type of enzyme used to ratchet the polymer, whether the polymer is being pushed or pulled through the pore by the enzyme, pH, salt concentration and the type of nucleoside triphosphate present. The duration of a state may vary typically between 0.5 ms and 3 s, depending on the biochemical analysis system 1, and for any given nanopore system, having some random variation between states. The expected distribution of durations may be determined experimentally for any given biochemical analysis system 1.

The extent to which a given biochemical analysis system 1 provides measurements that are dependent on k-mers and the size of the k-mers may be examined experimentally. Possible approaches to this are disclosed in WO-2013/041878.

Reverting to the biochemical analysis system 1 may take electrical measurements of types other than current measurements of ion current through a nanopore as described above.

Other possible electrical measurement include: current measurements, impedance measurements, tunneling measurements (for example as disclosed in Ivanov A P et al., Nano Lett. 2011 Jan. 12; 11(1):279-85), and field effect transistor (FET) measurements (for example as disclosed in WO2005/124888).

Reverting to FIG. 1, the arrangement of the electronic circuit 4 will now be discussed. The electronic circuit 4 is connected to the sensor electrode 22 in respect of each sensor element 30 and to the common electrode 25. The electronic circuit 4 may have an overall arrangement as described in WO 2011/067559. The electronic circuit 4 is arranged as follows to control the application of bias voltages across each sensor element 3 and to take the measurements from each sensor element 3.

Figure 5:
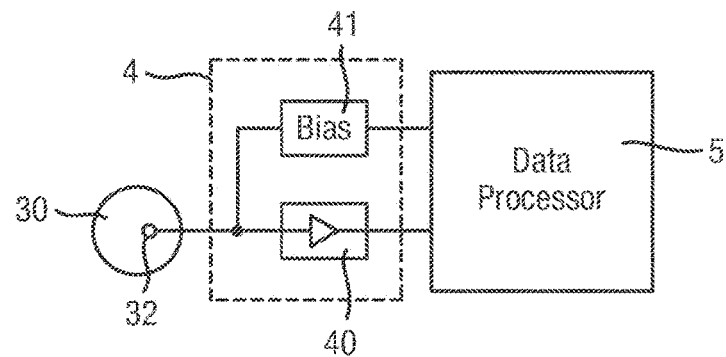
FIG. 5 is a diagram of the electronic circuit of the system in a first arrangement.

A first arrangement for the electronic circuit 4 is illustrated in FIG. 5 which shows components in respect of a single sensor element 30 that are replicated for each one of the sensor elements 30. In this first arrangement, the electronic circuit 4 includes a detection channel 40 and a bias control circuit 41 each connected to the sensor electrode 22 of the sensor element 30.

The detection channel 40 takes measurements from the sensor electrode 22. The detection channel 40 is arranged to amplify the electrical signals from the sensor electrode 22. The detection channel 40 is therefore designed to amplify very small currents with sufficient resolution to detect the characteristic changes caused by the interaction of interest. The detection channel 40 is also designed with a sufficiently high bandwidth to provide the time resolution needed to detect each such interaction. These constraints require sensitive and therefore expensive components. Specifically, the detection channel 40 may be arranged as described in detail in WO-2010/122293 or WO 2011/067559 to each of which reference is made and each of which is incorporated herein by reference.

The bias control circuit 41 supplies a bias voltage to the sensor electrode 22 for biasing the sensor electrode 22 with respect to the input of the detection channel 40.

During normal operation, the bias voltage supplied by the bias control circuit 41 is selected to enable translocation of a polymer through the pore 32. Such a bias voltage may typically be of a level up to −200 mV.

The bias voltage supplied by the bias control circuit 41 may also be selected so that it is sufficient to eject the translocating from the pore 32. By causing the bias control circuit 41 to supply such a bias voltage, the sensor element 30 is operable to eject a polymer that is translocating through the pore 32. To ensure reliable ejection, the bias voltage is typically a reverse bias, although that is not always essential. When this bias voltage is applied, the input to the detection circuit 40 is designed to remain at a constant bias potential even when presented with a negative current (of similar magnitude to the normal current, typically of magnitude −50 pA to −100 pA).

Figure 6:
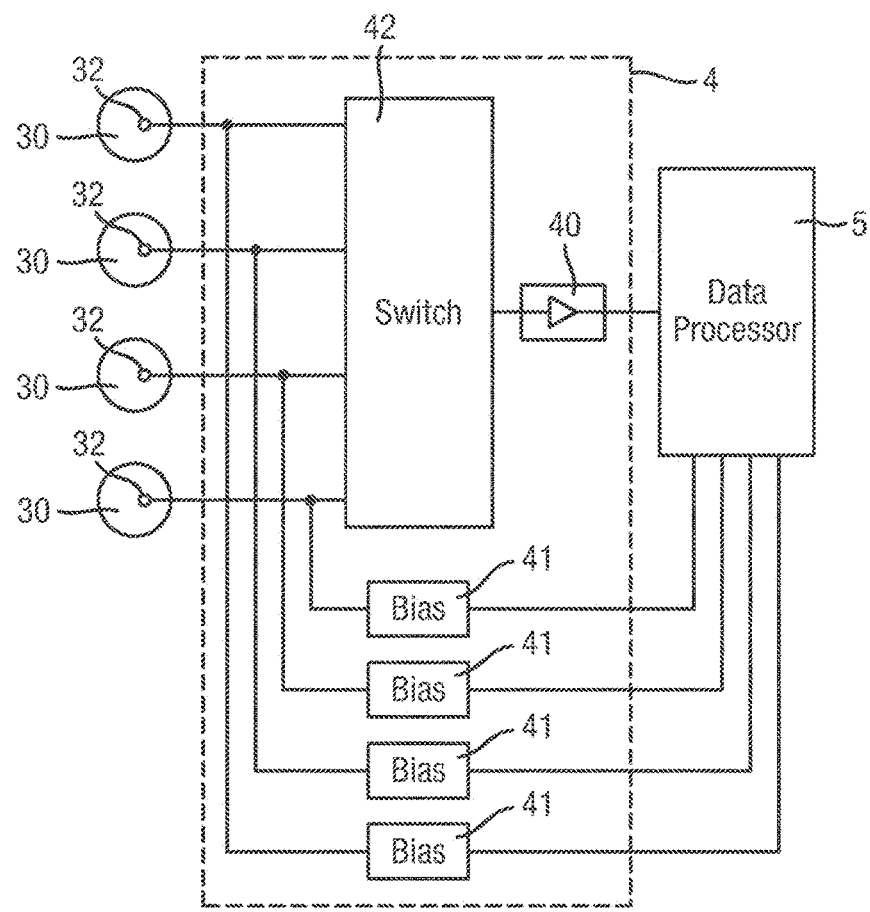
FIG. 6 is a diagram of the electronic circuit of the system in a second arrangement.

The first arrangement for the electronic circuit 4 illustrated in FIG. 5 requires a separate detection channel 40 for each sensor element 30 which is expensive to implement. A second arrangement for the electronic circuit 4 which reduces the number of detection channels 40 is illustrated in FIG. 6.

In this arrangement, the number of sensor elements 30 in the array is greater than the number of detection channels 40 and the biochemical sensing system is operable to take measurements of a polymer from sensor elements selected in an multiplexed manner, in particular an electrically multiplexed manner. This is achieved by providing a switch arrangement 42 between the sensor electrodes 23 of the sensor elements 30 and the detection channels 40. FIG. 6 shows a simplified example with four sensor cells 30 and two detection channels 40, but the number of sensor cells 30 and detection channels 40 can by greater, typically much greater. For example, for some applications, the sensor device 2 might comprise a total of 4096 sensor elements 30 and 1024 detection channels 40.

The switch arrangement 42 may be arranged as described in detail in WO-2010/122293. For example, the switch arrangement 42 may comprise plural 1-to-N multiplexers each connected to a group of N sensor elements 30 and may include appropriate hardware such as a latch to select the state of the switching.

Thus, by switching of the switch arrangement 42, the biochemical analysis system 1 may be operated to take measurements of a polymer from sensor elements 30 selected in an electrically multiplexed manner.

The switch arrangement 42 may be controlled in the manner described in WO-2010/122293 to selectively connect the detection channels 40 to respective sensor elements 30 that have acceptable quality of performance on the basis of the amplified electrical signals that are output from the detection channels 40, but in addition the switching arrangement is controlled as described further below.

As in the first arrangement, this second arrangement also includes a bias control circuit 41 in respect of each sensor element 30.

Although in this example, the sensor elements 30 are selected in an electrically multiplexed manner, other types of biochemical analysis system 1 could be configured to switch between sensor elements in a spatially multiplexed manner, for example by movement of a probe used to take electrical measurements, or by control of an optical system used to take optical measurements from the different spatial locations of different sensor elements 30.

The data processor 5 connected to the electronic circuit 4 is arranged as follows. The data processor 5 may be a computer apparatus running an appropriate program, may be implemented by a dedicated hardware device, or may be implemented by any combination thereof. The computer apparatus, where used, may be any type of computer system but is typically of conventional construction. The computer program may be written in any suitable programming language. The computer program may be stored on a computer-readable storage medium, which may be of any type, for example: a recording medium which is insertable into a drive of the computing system and which may store information magnetically, optically or opto-magnetically; a fixed recording medium of the computer system such as a hard drive; or a computer memory. The data processor 5 may comprise a card to be plugged into a computer such as a desktop or laptop. The data used by the data processor 5 may be stored in a memory 10 thereof in a conventional manner.

The data processor 5 controls the operation of the electronic circuit 3. As well as controlling the operation of the detection channels 41, the data processor controls the bias control circuits 41 and controls the switching of the switch arrangement 31. The data processor 5 also receives and processes the series of measurements from each detection channel 40. The data processor 5 stores and analyses the series of measurements, as described further below.

The data processor 5 controls the bias control circuits 41 to apply bias voltages that are sufficient to enable translocation of polymers through the pores 32 of the sensor elements 30. This operation of the biochemical sensor element 41 allows collection of series of measurements from different sensor elements 30 which may be analysed by the data processor 5, or by another data processing unit, to estimate the sequence of polymer units in a polymer, for example using techniques as described in WO-2013/041878. Data from different sensor elements 30 may be collected and combined.

The data processor 5 receives and analyses the series of raw measurements 11 taken by the sensor device 2, and supplied from the electronic circuit 4. The data processor 5 may also provide control signals to the electronic circuit 5, for example to select the voltage applied across the biological pore 1 in the sensor device 2. The series of raw measurements 11 may be supplied over any suitable connection, for example a direct connection in the case that the data processor 5 and the sensor device 2 are physically located together, or any type of network connection in the case that the data processor 5 and the sensor device 2 are physically remote from each other.

There will now be described a method shown in FIG. 7 of controlling the biochemical analysis system 1 to analyse polymers. This method is in accordance with the first aspect of the present invention and is performed in a manner that increases the speed of analysis by rejecting the polymer no further analysis is needed. This method is implemented in the data processor 5. This method is performed in parallel in respect of each sensor element 30 from which a series of measurements is taken, that is every sensor element 30 in the first arrangement for the electronic circuit 4, and each sensor element 30 that is connected to a detection channel 40 by the switch arrangement 42 in the second arrangement for the electronic circuit 4.

In step C1, the biochemical analysis system 1 is operated by controlling the bias control circuit 30 to apply a bias voltage across the pore 32 of the sensor element 30 that is sufficient to enable translocation of polymer. Based on the output signal from the detection channel 40, translocation is detected and a measurements start to be taken. A series of measurements is taken over time.

In some cases, the following steps operate on the series of raw measurements 11 taken by the sensor device 2, i.e. being a series of measurements of the type described above comprising successive groups of plural measurements that are dependent on the same k-mer without a priori knowledge of number of measurements in any group.

Figure 8:
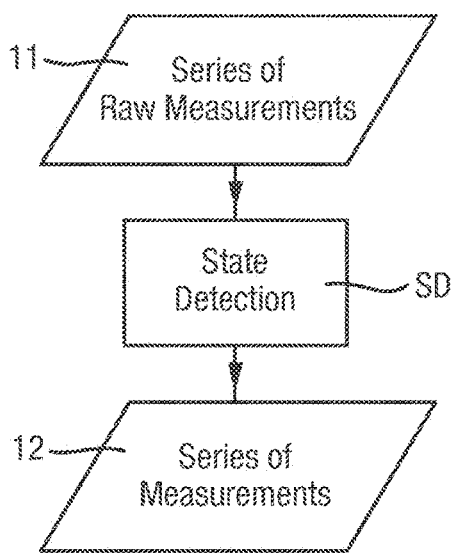
FIG. 8 is a flow chart of a state detection step.

In other cases, as shown in FIG. 8, the raw measurements 11 are pre-processed using a state detection step SD to derive a series of measurements 12 that are used in the following steps instead of the raw measurements.

In such a state detection step SD, the series of raw measurements 11 is processed to identify successive groups of raw measurements and to derive a series of measurements 12 consisting of a predetermined number of measurements in respect of each identified group. Thus, a series of measurements 12 is derived in respect of each sequence of polymer units that is measured. The purpose of the state detection step SD is to reduce the series of raw measurements to a predetermined number of measurements associated with each k-mer to simplify the subsequent analysis. For example a noisy step wave signal, as shown in FIG. 4 may be reduced to states where a single measurement associated with each state may be the mean current. This state may be termed a level.

Figure 9:
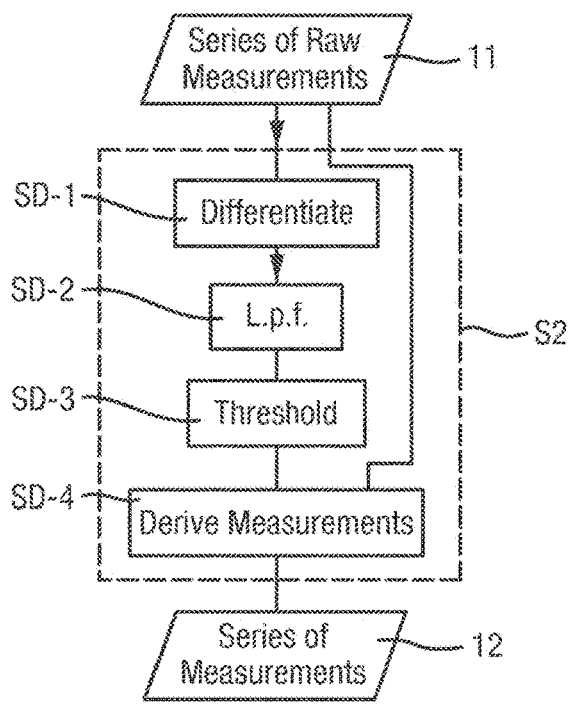
FIG. 9 is a detailed flow chart of an example of the state detection step.

FIG. 9 shows an example of such a state detection step SD that looks for short-term increases in the derivative of the series of raw measurements 11 as follows.

In step SD-1, the series of raw measurements 11 is differentiated to derive its derivative.

In step SD-2, the derivative from step SD-1 is subjected to low-pass filtering to suppress high-frequency noise, which the differentiation in step SD-1 tends to amplify.

In step SD-3, the filtered derivative from step SD-2 is thresholded to detect transition points between the groups of measurements, and thereby identify the groups of raw measurements.

In step SD-4, a predetermined number of measurements is derived from each group of raw measurements identified in step SD-3. The measurements output from step SD-4 form the series of measurements 12.

The predetermined number of measurements may be one or more.

In the simplest approach, a single measurement is derived from each group of raw measurements, for example the mean, median, standard deviation or number, of raw measurements in each identified group.

In other approaches, a predetermined plural number of measurements of different natures are derived from each group, for example any two or more of the mean, median, standard deviation or number of raw measurements in each identified group. In that case, the a predetermined plural number of measurements of different natures are taken to be dependent on the same k-mer since they are different measures of the same group of raw measurements.

The state detection step SD may use different methods from that shown in FIG. 9. For example a common simplification of method shown in FIG. 9 is to use a sliding window analysis which compares the means of two adjacent windows of data. A threshold can then be either put directly on the difference in mean, or can be set based on the variance of the data points in the two windows (for example, by calculating Student's t-statistic). A particular advantage of these methods is that they can be applied without imposing many assumptions on the data.

Other information associated with the measured levels can be stored for use later in the analysis. Such information may include without limitation any of: the variance of the signal; asymmetry information; the confidence of the observation; the length of the group.

Figure 10:
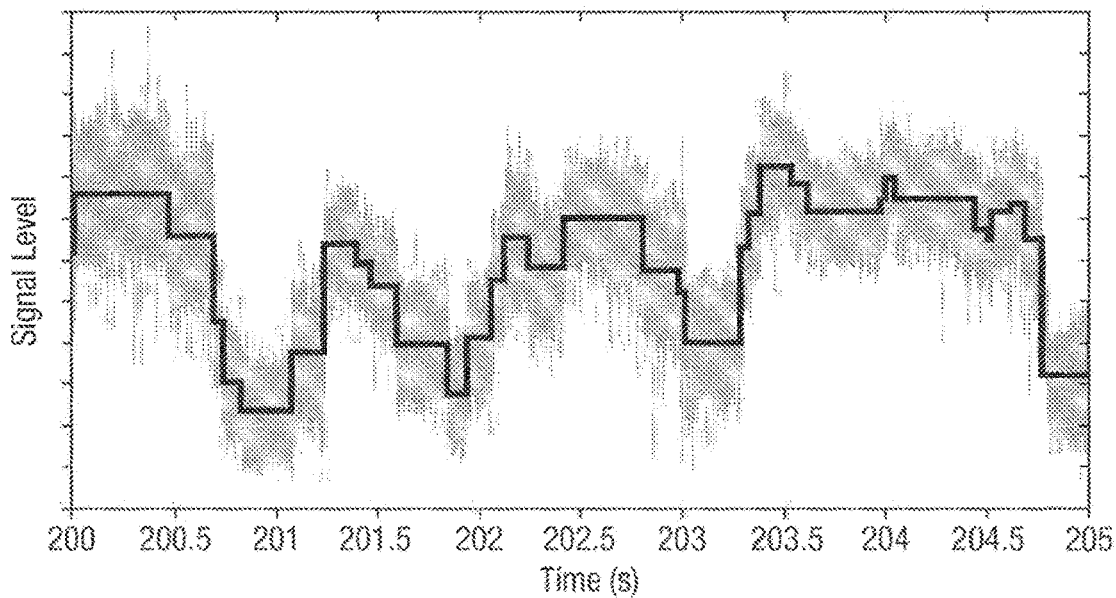
FIG. 10 is a plot of a series of raw measurements subject to the state detection step and of the resultant series of measurements.

By way of example, FIG. 10 illustrates an experimentally determined series of raw measurements 11 reduced by a moving window t-test. In particular, FIG. 10 shows the series of raw measurements 11 as the light line. Levels following state detection are shown overlaid as the dark line.

Step C2 is performed when a polymer has partially translocated through the nanopore, i.e. during the translocation. At this time, the series of measurements taken from the polymer during the partial translocation is collected for analysis, which is referred to herein as a "chunk" of measurements. Step C2 may be performed after a predetermined number of measurements have been taken so that the chunk of measurements is of predefined size, or may alternatively after a predetermined amount of time. In the former case, the size of the chunk of measurements may be defined by parameters that are initialised at the start of a run, but are changed dynamically so that the size of the chunk of measurements changes.

In step C3, the chunk of measurements collected in step C2 is analysed. This analysis uses reference data 50. As discussed in more detail below, the reference data 50 is derived from at least one reference sequence of polymer units. The analysis performed in step C3 provides a measure of similarity between (a) the sequence of polymer units of the partially translocated polymer from which measurements have been taken and (b) the one reference sequence.

Various techniques for performing this analysis are possible, some examples of which are described below.

The measure of similarity may indicate similarity with the entirety of the reference sequence, or with a portion of the reference sequence, depending on the application. The technique applied in step C3 to derive the measure of similarity may be chosen accordingly, for example being a global or a local method.

Also, the measure of similarity may indicate the similarity by various different metrics, provided that it provides in general terms a measure of how similar the sequences are. Some examples of specific measures of similarity that may be determined from the sequences in different ways are set out below.

In step C4, a decision is made responsive to the measure of similarity determined in step C3 either (a) to reject the polymer being measured, (b) that further measurements are needed to make a decision, or (c) to continue taking measurements until the end of the polymer.

If the decision made in step C4 is (a) to reject the polymer being measured, then the method proceeds to step C5 wherein the biochemical analysis system 1 is controlled to reject the polymer, so that measurements can be taken from a further polymer.

Step C5 is performed differently as between the first and second arrangement of the electronic circuit 4, as follows.

In the case of the first arrangement of the electronic circuit 4, then in step C5 the bias control circuit 30 is controlled to apply a bias voltage across the pore 32 of the sensor element 30 that is sufficient to eject the polymer currently being translocated. This ejects the polymer and thereby makes the pore 32 available to receive a further polymer. After ejection such ejection in step C5, the method returns to step C1 and so the bias control circuit 30 is controlled to apply a bias voltage across the pore 32 of the sensor element 30 that is sufficient to enable translocation of a further polymer through the pore 32.

In the case of the second arrangement of the electronic circuit 4, then in step C5 the biochemical analysis system 1 is caused to cease taking measurements from the currently selected sensor element 30 by controlling the switch arrangement 42 to disconnect the detection channel 40 that is currently connected to the sensor element 30 and to selectively connect that detection channel 40 to a different sensor element 30. At the same time, in step C5, the bias control circuit 30 is controlled to apply a bias voltage across the pore 32 of the sensor element 30 that is sufficient to eject the polymer currently being translocated through the currently selected sensor element 30 so that sensor element 30 is available to receive a further polymer in the future.

The method then returns to step C1 which is applied to the newly selected sensor element 30 so that the biochemical analysis system 1 starts taking measurements therefrom.

If the decision made in step C4 is (b) that further measurements are needed to make a decision, then the method reverts to step C2. Thus, measurements of the translocating polymer continue to be taken until a chunk of measurements is next collected in step C2 and analysed in step C3. The chunk of measurements collected when step C2 is performed again may be solely the new measurements to be analysed in isolation, or may be the new measurements combined with previous chunks of measurements.

If the decision made in step C4 is (c) to continue taking measurements until the end of the polymer, then the method proceeds to step C6 without repeating the steps C2 and C3 so that no further chunks of data are analysed. In step C6, the sensor element 1 continues to be operated so that measurements continue to be taken until the end of the polymer. Thereafter the method reverts to step C1, so that a further polymer may be analysed.

The degree of similarity, as indicated by the measure of similarity, that is used as the basis for the decision in step C4 may vary depending on the application and the nature of the reference sequence. Thus provided that the decision is responsive to the measure of similarity, there is in general no limitation on the degree of similarity that is used to make the different decisions.

Some examples of how the dependence on the measure of similarity might vary are as follows.

In applications where the reference sequence of polymer units is an unwanted sequence, and in step C4 a decision to reject the polymer is made to responsive to the measure of similarity indicating that the partially translocated polymer is the unwanted sequence, a relatively high degree of similarity may be used as the basis to reject the polymer. Similarly, the degree of similarity may vary depending on the nature of the reference sequence in the context of the application. Where it is intended to distinguish between similar sequences a higher degree of similarity may be required as the basis for the rejection.

Conversely, in applications where the reference sequence of polymer units from which the reference data 50 is derived is a target, and in step C4 a decision to reject the polymer is made to responsive to the measure of similarity indicating that the partially translocated polymer is not the target, a relatively low degree of similarity may be used as the basis to reject the polymer.

As another example, if the application is to determine whether a known gene from a known bacterium is present in a sample of various bacteria, the degree of similarity required to determine whether a polynucleotide has the same sequence as the target will be higher if the gene has a conserved sequence across different bacterial strains than if the sequence was not conserved.

Similarly in some of the embodiments of the invention the measure of similarity will equate to a degree of identity of a polymer to the target polymer, whereas in other embodiments the measure of similarity will equate to a probability that the polymer is the same as the target polymer.

The degree of similarity required as the basis for rejection may also be varied in dependence on the potential time saving, which is itself dependent on the application as described below. The false-positive rate that is acceptable may be dependent on the time saving. For example, where the potential time saving by rejecting an unwanted polymer is relatively high, it is acceptable to reject an increased proportion of polymers that are targets, provided that there is an overall time saving from rejection of polymers that are actually unwanted.

Figure 7:
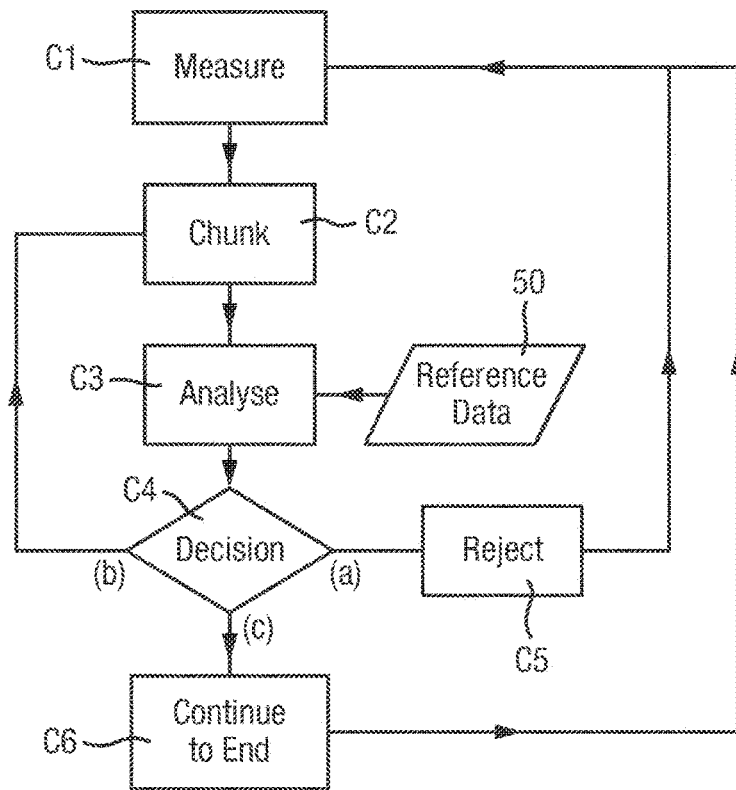
FIG. 7 is a flow chart of a method of controlling the biochemical analysis system to analyse polymers.

Reverting now to the method of FIG. 7, if at any point during the taking of measurements of a polymer it is detected that measurements are no longer being taken, indicating that the end of the polymer has been reached, then the method reverts immediately to step C1, so that a further polymer may be analysed. After so taking measurements of the entire polymer, those measurements may be analysed as disclosed in WO-2013/041878, for example to derive an estimate of the sequence of polymer units.

The source of the reference data 50 may vary depending on the application. The reference data 50 may be generated from the reference sequence of polymer units or from measurements taken from the reference sequence of polymer units.

In some applications, the reference data 50 may be pre-stored having been generated previously. In other applications, the reference data 50 is generated at the time the method is performed.

The reference data 50 may be provided in respect of a single reference sequence of polymer units or plural reference sequences of polymer units. In the latter case, either step C3 is performed in respect of each sequence or else one of the plural reference sequences is selected for use in step C3. In the latter case, the selection may be made based on various criteria, depending on the application. For example, the reference data 50 may be applicable to different types of biochemical analysis system 1 (e.g. different nanopores) and/or ambient conditions, in which case the selection of the reference model 70 described below is based on the type of biochemical analysis system 1 actually used and/or the actual ambient conditions.

The method shown in FIG. 7 may be varied, depending on the application. For example, in some variations, the decision in step C4 is never (c) to continue taking measurements until the end of the polymer, so that the method repeatedly collects and analyses chunks of measurements until the end of the polymer.

In another variation, in step C3 instead of using the reference data 50 and determining the measure of similarity, the decision in step C4 to reject the polymer may be based on other analysis of the series of measurements, in general on any analysis of the chunk of measurements.

In one possibility, step C3 may analyse whether the chunk of measurements are of insufficient quality, for example having a noise level that exceeds a threshold, having the wrong scaling, or being characteristic of a polymer that is damaged.

The decision in step C4 is made on the basis of that analysis, thereby rejecting the polymer on the basis on an internal quality control check. This still involves making a decision to reject a polymer based on a chunk of measurements, that is a series of measurements taken from the polymer during the partial translocation, and so is in contrast to that ejecting a polymer which causes a blockade, in which case the polymer is no longer translocating, so k-mer dependent measurements are not taken.

Figure 11:
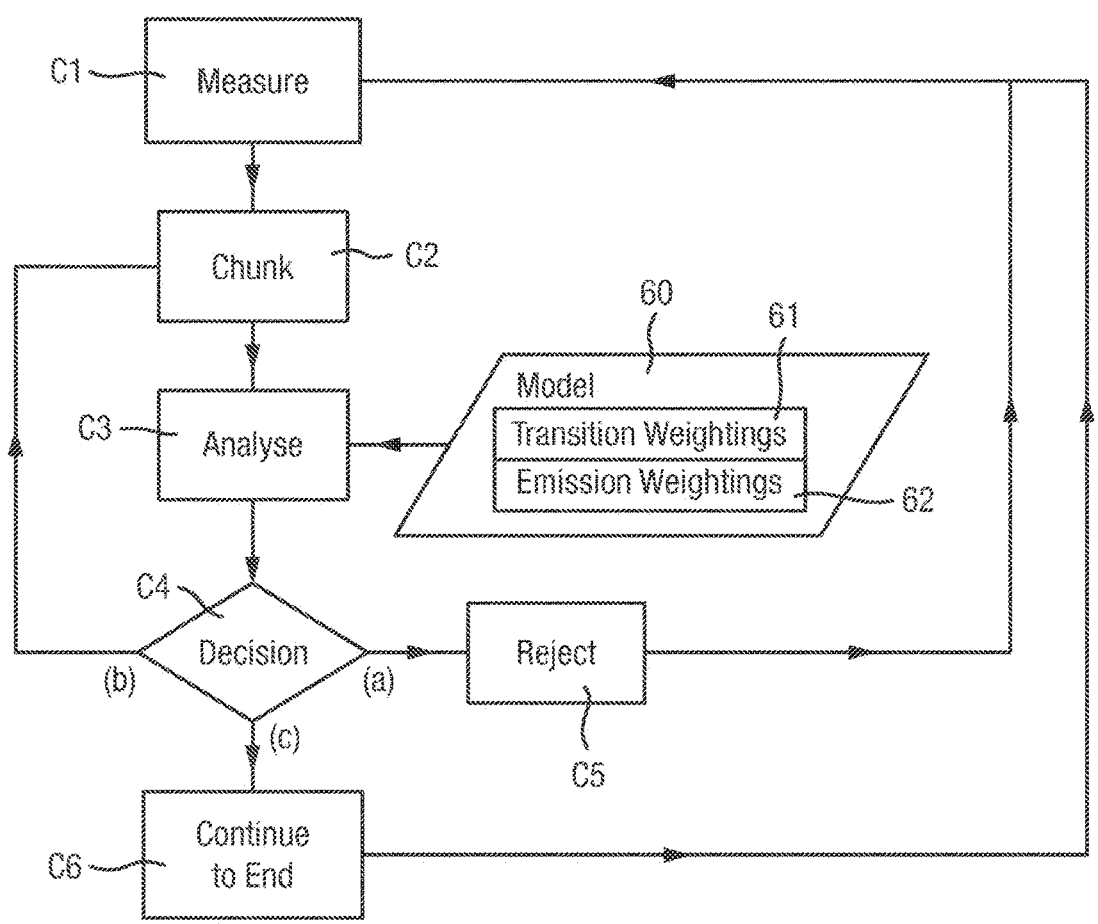
FIG. 11 is a flow chart of an alternative method of controlling the biochemical analysis system to analyse polymers.

In another possibility in which the method is in accordance with the second aspect of the present invention, the method is modified as shown in FIG. 11. This method is the same as that of FIG. 7 except that step C3 is modified. In step C3, instead of using the reference data 50 derived from at least one reference sequence of polymer units and determining the measure of similarity, there is used a general model 60 that treats the measurements as observations of a series of k-mer states of different possible types and comprises: transition weightings 61, in respect of each transition between successive k-mer states in the series of k-mer states, for possible transitions between the possible types of k-mer state; and emission weightings 62, in respect of each type of k-mer state that represent the chances of observing given values of measurements for that k-mer. Step C3 is modified so as to comprise deriving a measure of fit to the reference model 60.

Figure 13:
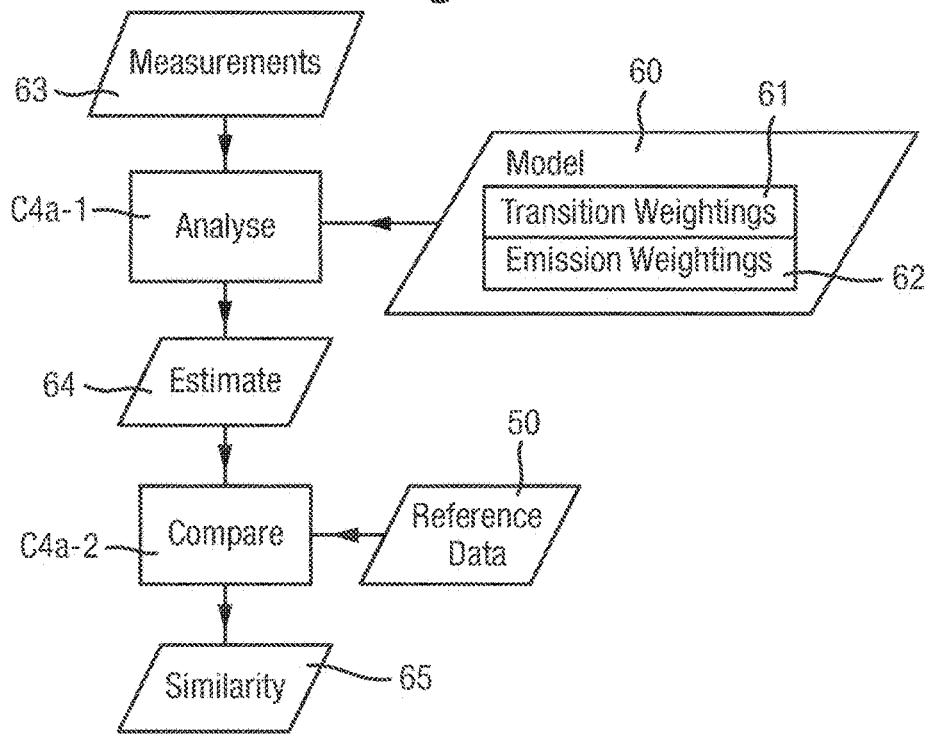
FIGS. 13 to 16 are flow charts of different methods for analysing reference data of different forms.

The general model 60 may of the type described in WO-2013/041878. Reference is made to WO-2013/041878 for the details of the model. The general model 60 described further below with reference to FIG. 13. The measure of fit is derived, for example as the likelihood of the measurements being observed from the most likely sequence of k-mer states. Such a measure of fit indicates the quality of the measurements.

When step C3 is modified in this way, the decision in step C4 is made on the basis of that measure of fit, thereby rejecting the polymer on the basis on an internal quality control check.

Thus, the method causes a polymer to be rejected if the similarity to the reference sequence of polymer units indicates no further analysis of the polymer is needed or if the measurements taken from that polymer are of poor quality as determined by the model such that further translocation and measurement is not warranted. The extent to which data is indicated by the model as not being sufficiently good depends upon the complexity of the model itself. For example a more complex model may have parameters which can address some of the conditions that could give rise to a rejection.

Conditions that might give rise to rejection may include for example: drift in the signal that is unacceptable; high noise; un-modelled behaviour; irregular system errors such as temperature fluctuation; and/or errors due to the electro-physical system.

For example, one possibility is that polymer or other debris has become lodged in the nanopore producing a slowly varying, rather static, current flow. The model generally expects well separated (piecewise constant in time) steps in the data, and so such measurements will have a poor measure of fit to the model.

A second possibility is transient noise, for example large changes in current between otherwise closely group steps. If such noise is occurring with high frequency the data is potentially of little use for practical purposes. The measure of fit to the model will be low due to the high frequency of unexpected measurements.

These "errors" may occur in a non-transitory fashion. Indeed it is often observed that sections of measurements appear offset in their average current with respect to neighbouring sections. A possible explanation for this is a change in conformation of the pore and the polymer molecule. Regardless of the cause, such behaviour is not captured in the model, and so for practical purposes the data is of little use.

The affect of such errors could be mitigated to a certain extent by increasing the complexity of the model. However this can be undesirable and may result in raising the computation cost of modelling the data and decoding the polymer sequence.

As a consequence of rejecting such polymer strands, only those polymer sequences with strong homology to that which the model's transition and emission weighting are derived will give rise to measurements which have a good measure of fit to the model.

After finishing taking measurements of the entire polymer, those measurements may be analysed as disclosed in WO-2013/041878, for example to derive an estimate of the sequence of polymer units.

The alternative methods of FIGS. 7 and 11 may be applied independently or in combination, in which case they may be applied simultaneously (for example with step C3 of both methods being performed in parallel, and the other steps being performed in common) or sequentially (for example performing the method of FIG. 11 prior to the method of FIG. 7).

There will now be described a method shown in FIG. 12 of controlling the biochemical analysis system 1 to sort polymers. This method is in accordance with the third aspect of the present invention. In this case, the sample chamber 24 contains a sample comprising the polymers, which may be of different types, and the wells 21 act as collection chambers for collecting the sorted polymers.

This method is implemented in the data processor 5. This method is performed in parallel in respect of plural sensor elements 30 in parallel, for example every sensor element 30 in the first arrangement for the electronic circuit 4, and each sensor element 30 that is connected to a detection channel 40 by the switch arrangement 42 in the second arrangement for the electronic circuit 4.

In step D1, the biochemical analysis system 1 is operated by controlling the bias control circuit 30 to apply a bias voltage across the pore 32 of the sensor element 30 that is sufficient to enable translocation of polymer. This causes a polymer to start translocation through the nanopore and during the translocation the following steps are performed. Based on the output signal from the detection channel 40, translocation is detected and a measurements start to be taken. A series of measurements of the polymer is taken from the sensor element 30 over time.

In some cases, the following steps operate on the series of raw measurements 11 taken by the sensor device 2, i.e. being a series of measurements of the type described above comprising successive groups of plural measurements that are dependent on the same k-mer without a priori knowledge of number of measurements in any group.

In other cases, the raw measurements 11 are pre-processed using a state detection step SD to derive a series of measurements 12 that are used in the following steps instead of the raw measurements. The state detection state SD may be performed in the same manner as in step C1 as described above with reference to FIGS. 8 and 9.

Step D2 is performed when a polymer has partially translocated through the nanopore, i.e. during the translocation. At this time, the series of measurements taken from the polymer during the partial translocation is collected for analysis, which is referred to herein as a "chunk" of measurements. Step D2 may be performed after a predetermined number of measurements have been taken so that the chunk of measurements is of predefined size, or may alternatively after a predetermined amount of time. In the former case, the size of the chunk of measurements may be defined by parameters that are initialised at the start of a run, but are changed dynamically so that the size of the chunk of measurements changes.

In step D3, the chunk of measurements collected in step D2 is analysed. This analysis uses reference data 50. As discussed in more detail below, the reference data 50 is derived from at least one reference sequence of polymer units. The analysis performed in step D3 provides a measure of similarity between (a) the sequence of polymer units of the partially translocated polymer from which measurements have been taken and (b) the one reference sequence. Various techniques for performing this analysis are possible, some examples of which are described below.

The measure of similarity may indicate similarity with the entirety of the reference sequence, or with a portion of the reference sequence, depending on the application. The technique applied in step D3 to derive the measure of similarity may be chosen accordingly, for example being a global or a local method.

Also, the measure of similarity may indicate the similarity by various different metrics, provided that it provides in general terms a measure of how similar the sequences are. Some examples of specific measures of similarity that may be determined from the sequences in different ways are set out below.

In step D4, a decision is made in dependence on the measure of similarity determined in step D3 either, (a) that further measurements are needed to make a decision, (b) to complete the translocation of the polymer into the well 21, or (c) to eject the polymer being measured back into the sample chamber 24. If the decision made in step D4 is (a) that further measurements are needed to make a decision, then the method reverts to step D2. Thus, measurements of the translocating polymer continue to be taken until a chunk of measurements is next collected in step D2 and analysed in step D3. The chunk of measurements collected when step D2 is performed again may be solely the new measurements to be analysed in isolation, or may be the new measurements combined with previous chunks of measurements.

If the decision made in step D4 is (b) to complete the translocation of the polymer into the well 21, then the method proceeds to step D6 without repeating the steps D2 and D3 so that no further no further analysis of measurements is performed.

In step D6, the translocation of the polymer into the well 21 is completed. As a result the polymer is collected in the well 21.

Step D6 may be performed by continuing to apply the same bias voltage across the pore 32 of the sensor element 30 that enables translocation of polymer.

Alternatively, in step D6, the bias voltage may be changed to perform the remainder of the translocation of the polymer at an increased rate to reduce the time taken for translocation. This is advantageous because it increases the overall speed of the sorting process. It is acceptable to increase the translocation speed, because the polymer no longer needs to be analysed. Typically, the change in bias voltage may be an increase. In a typical system, the increase may be significant. For example in one embodiment, the translocation speed may be increased from around 30 bases per second to around 10,000 bases per second. The possibility of changing the translocation speed may depend on the configuration of the sensor element. For example, where a polymer binding moiety, for example an enzyme, is used to control the translocation, this may depend on the a polymer binding moiety used. Advantageously, a polymer binding moiety that can control the rate may be selected.

During step D6, the sensor element 1 may continue to be operated so that measurements continue to be taken until the end of the polymer, but this is optional as there is no need to determine the remainder of the sequence.

After step D6, the method reverts to step D1, so that a further polymer may be translocated.

If the decision made in step D4 is (c) to eject the polymer, then the method proceeds to step D5 wherein the biochemical analysis system 1 is controlled to eject the polymer being measured back into the sample chamber 24, so that measurements can be taken from a further polymer.

In step D5, the bias control circuit 30 is controlled to apply a bias voltage across the pore 32 of the sensor element 30 that is sufficient to eject the polymer currently being translocated. This ejects the polymer and thereby makes the pore 32 available to receive a further polymer. After ejection such ejection in step D5, the method returns to step D1 and so the bias control circuit 30 is controlled to apply a bias voltage across the pore 32 of the sensor element 30 that is sufficient to enable translocation of a further polymer through the pore 32.

On reverting to step D1, the method repeats. Repeated performance of the method causes successive polymers from the sample chamber 24 to be translocated and processed.

Thus, the method makes use of the measure of similarity provided by the analysis of the series of measurements taken from the polymer during the partial translocation as the basis for whether or notusccessive polymers are collected in the well 21. In this manner, polymers from the sample in the sample chamber 24 are sorted and desired polymers are selectively collected in the well 21.

The collected polymers may be recovered. This may be done after the method has been run repeatedly, by removing the sample from the sample chamber 24 and then recovering the polymers from the wells 21. Alternatively, this could be done during translocation of polymers from the sample, for example by providing the biochemical analysis system 1 with a fluidics system that extracts the polymers from the wells 21.

The method may be applied to a wide range of applications. For example, the method could be applied to polymers that are polynucleotides, for example viral genomes or plasmids. A viral genome typically has a length of order 10-15 kB (kilobases) and a plasmid typically has a length of order 4 kB. In such examples, the polynucleotides would not have to be fragmented and could be collected whole. The collected viral genome or plasmid could be used in any way, for example to transfect a cell. Transfection is the process of introducing DNA into a cell nucleus and is an important tool used in studies investigating gene function and the modulation of gene expression, thus contributing to the advancement of basic cellular research, drug discovery, and target validation. RNA and proteins may also be transfected.

The degree of similarity, as indicated by the measure of similarity, that is used as the basis for the decision in step D4 may vary depending on the application and the nature of the reference sequence. Thus provided that the decision is dependent on the measure of similarity, there is in general no limitation on the degree of similarity that is used to make the different decisions.

Some examples of how the dependence on the measure of similarity might vary are as follows.

In many applications, the reference sequence of polymer units from which the reference data 50 is derived is a wanted sequence. In that case, in step D4 a decision to complete the translocation is made to responsive to the measure of similarity indicating that the partially translocated polymer is the wanted sequence, a relatively high degree of similarity may be used as the basis to complete the translocation.

However, this is not essential. In some applications, the reference sequence of polymer units is an unwanted sequence. In that case, in step D4 a decision to complete the translocation is made to responsive to the measure of similarity indicating that the partially translocated polymer is not the unwanted sequence.

Similarly, the degree of similarity may vary depending on the nature of the reference sequence in the context of the application. Where it is intended to distinguish between similar sequences a higher degree of similarity may be required as the basis for the rejection.

The method may be performed using the same reference data 50 and the same criteria in step D4 in respect of each sensor element 30. In that case, each well 21 collects the same polymers in parallel.

Alternatively, the method may be performed to collect different polymers in different wells 21. In this case, differential sorting is performed. In one example of this, different reference data 50 is used in respect of different sensor elements 30. In another example of this, the same reference data 50 is used in respect of different sensor elements 30, but step D4 is performed with different dependence on the measure of similarity in respect of different sensor elements.

Figure 12:
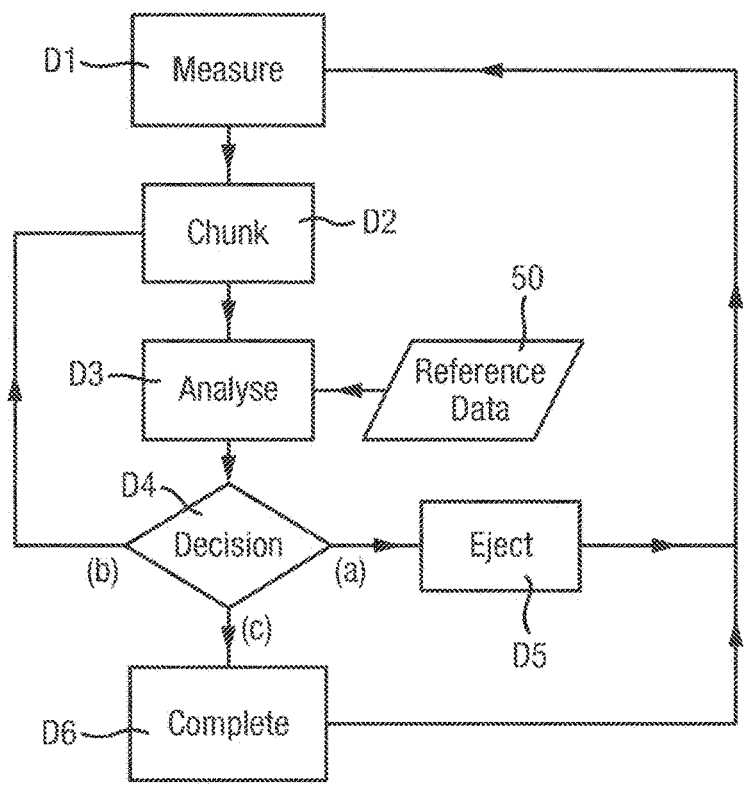
FIG. 12 is a flow chart of a method of controlling the biochemical analysis system to sort polymers.

The methods shown in FIGS. 7, 11 and 12 may be varied, depending on the application.

A variety of different types of reference sequence of polymer units may be used, depending on the application. Without limitation, where the polymer is a polynucleotide, the reference sequence of polymer units may comprise one or more reference genomes or a region of interest of the one or more genomes to which the measurement is compared.

The source of the reference data 50 may vary depending on the application. The reference data may be generated from the reference sequence of polymer units or from measurements taken from the reference sequence of polymer units.

In some applications, the reference data 50 may be pre-stored having been generated previously. In other applications, the reference data 50 is generated at the time the method is performed.

The reference data 50 may be provided in respect of a single reference sequence of polymer units or plural reference sequences of polymer units. In the latter case, either step D3 is performed in respect of each sequence or else one of the plural reference sequences is selected for use in step D3. In the latter case, the selection may be made based on various criteria, depending on the application. For example, the reference data 50 may be applicable to different types of biochemical analysis system 1 (e.g. different nanopores) and/or ambient conditions, in which case the selection of the reference model 70 described below is based on the type of biochemical analysis system 1 actually used and/or the actual ambient conditions.

The biochemical analysis system 1 described above is an example of a biochemical analysis system that comprises an array of sensor elements that each comprise a nanopore. However, the methods described above may be applied generally to any biochemical analysis system that is operable to take successive measurements of polymers, possibly without the use of nanopores.

An example of such a biochemical analysis system that does not comprise a nanopore is a scanning probe microscope, that may be an atomic force microscope (AFM), a scanning tunneling microscope (STM) or another form of scanning microscope. In such a case, the biochemical analysis system may be operable to take successive measurements of polymers selected in a spatially multiplexed manner. For example, the polymers may be disposed on a substrate in different spatial locations and the spatial multiplexing may be provided by movement of the probe of the scanning probe microscope.

In the case where the reader is an AFM, the resolution of the AFM tip may be less fine than the dimensions of an individual polymer unit. As such the measurement may be a function of multiple polymer units. The AFM tip may be functionalised to interact with the polymer units in an alternative manner to if it were not functionalised. The AFM may be operated in contact mode, non-contact mode, tapping mode or any other mode.

In the case where the reader is a STM the resolution of the measurement may be less fine than the dimensions of an individual polymer unit such that the measurement is a function of multiple polymer units. The STM may be operated conventionally or to make a spectroscopic measurement (STS) or in any other mode.

The form of the reference data 50, as used in any of the methods described above will now be discussed. The reference data 50 may take various forms that are derived from the reference sequence of polymer units in different ways. The analysis performed in step C4 or D4 to provide the measure of similarity is dependent on the form of the reference data 50. Some non-limitative examples will now be described.

In a first example, the reference data 50 represents the identity of the polymer units of the at least one reference sequence. In that case, step C4 or D4 comprises the process shown in FIG. 13, as follows.

In step C4a-1, the chunk of measurements 63 is analysed to provide an estimate 64 of the identity of the polymer units of a sequence of polymer units of the partially translocated polymer. Step C4a-1 may in general be performed using any method for analysing the measurements taken by the biochemical analysis system.

Step C4a-1 may be performed in particular using the method described in detail in WO-2013/041878, which is incorporated herein by reference. Reference is made to WO-2013/041878 for the details of the method, but a summary is given as follows.

This method makes reference to a general model 60 comprises transition weightings 61 and emission weightings 62 in respect of a series of k-mer states corresponding to the chunk of measurements 63.

The transition weightings 61 are provided in respect of each transition between successive k-mer states in the series of k-mer states. Each transition may be considered to be from an origin k-mer state to a destination k-mer state. The transition weightings 61 represent the relative weightings of possible transitions between the possible types of the k-mer state, that is from an origin k-mer state of any type to a destination k-mer state of any type. In general, this includes a weighting for a transition between two k-mer states of the same type.

The emission weightings 62 are provided in respect of each type of k-mer state. The emission weightings 62 are weightings for different measurements being observed when the k-mer state is of that type. Conceptually, the emission weightings 62 may be thought of as representing the chances of the chances of observing given values of measurements for that k-mer state, although they do not need to be probabilities.

Conceptually, the transition weightings 61 may be thought of as representing the chances of the possible transition, although they do not need to be probabilities. Therefore, the transition weightings 61 take account of the chance of the k-mer state on which the measurements depend transitioning between different k-mer states, which may be more or less likely depending on the types of the origin and destination k-mer states.

By way of example and without limitation, the model may be a HMM in which the transition weightings 61 and emission weightings 62 are probabilities.

Step C4a-1 uses the reference model 60 to derive an estimate 64 of the identity of the polymer units of a sequence of polymer units of the partially translocated polymer. This may be performed using known techniques that are applicable to the nature of the reference model 60. Typically, such techniques derive the estimate 64 based on the likelihood of the measurements predicted by the reference model 60 being observed from sequences of k-mer states. As described in WO-2013/041878, such techniques may be performed on the series of raw measurements 11 or the series of measurements 12.

Such methods may also provide a measure of fit of the measurements to the model, for example a quality score that indicates the likelihood of the measurements predicted by the reference model 60 being observed from the most likely sequence of k-mer states. Such measures are typically derived because they are used to derive the estimate 64.

As an example in the case that the general model 60 is an HMM, the analytical technique may be a known algorithm for solving the HMM, for example the Viterbi algorithm which is well known in the art. In that case, the estimate 64 is derived based on the likelihood predicted by the general model 60 being produced by overall sequences of k-mer states.

As another example in the in the case that the general model 60 is an HMM, the analytical technique may be of the type disclosed in Fariselli et al., "The posterior-Viterbi: a new decoding algorithm for hidden Markov models", Department of Biology, University of Casadio, archived in Cornell University, submitted 4 Jan. 2005. In this method, a posterior matrix (representing the probabilities that the measurements are observed from each k-mer state) and obtain a consistent path, being a path where neighbouring k-mer states are biased towards overlapping, rather than simply choosing the most likely k-mer state per event. In essence, this allows recovery of the same information as obtained directly from application of the Viterbi algorithm.

The above description is given in terms of a general model 60 that is a HMM in which the transition weightings 61 and emission weightings 62 are probabilities and method uses a probabilistic technique that refers to the general model 60. However, it is alternatively possible for the general model 60 to use a framework in which the transition weightings 61 and/or the emission weightings 62 are not probabilities but represent the chances of transitions or measurements in some other way. In this case, the method may use an analytical technique other than a probabilistic technique that is based on the likelihood predicted by the general model 60 of the series of measurements being produced by sequences of polymer units. The analytical technique may explicitly use a likelihood function, but in general this is not essential.

In step C4a-2, the estimate 64 is compared with the reference data 50 to provide the measure of similarity 65. This comparison may use any known technique for comparing two sequence of polymer units, typically being an alignment algorithm that derives an alignment mapping between the sequence of polymer units, together with a score for the accuracy of the alignment mapping which is therefore the measure of similarity 65. Any of a number of available fast alignment algorithms may be used, such as Smith-Waterman alignment algorithm, BLAST or derivatives thereof, or a k-mer counting technique.

This example of the form of the reference data 50 has the advantage that the process for deriving the measure of similarity 65 is rapid, but other forms of the reference data are possible.

Figure 14:
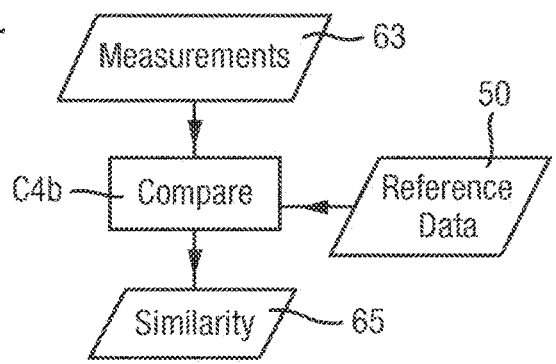

In a second example, the reference data 50 represents actual or simulated measurements taken by the biochemical analysis system 1. In that case, step C4 or D4 comprises the process shown in FIG. 14 which simply comprises step C4b of comparing the chunk of measurements 63, which in this case is taken from the series of raw measurements 11, with the reference data 50 to derive the measure of similarity 65. Any suitable comparison may be made, for example using a distance function to provide a measure of the distance between the two series of measurements, as the measure of similarity 65.

Figure 15:
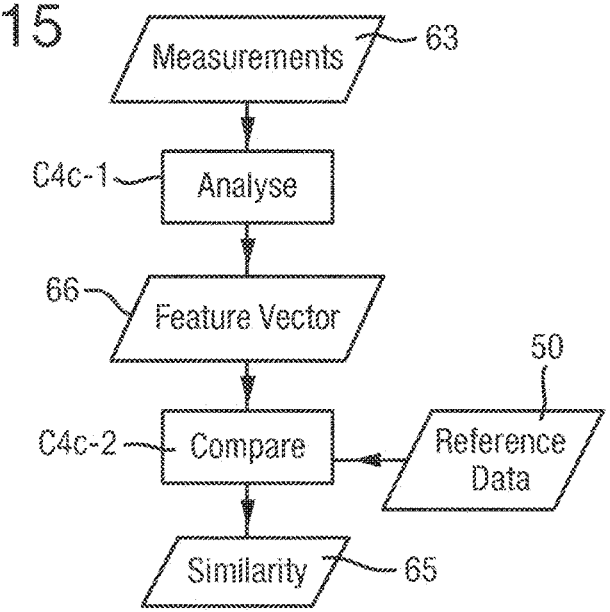

In a third example, the reference data 50 represents a feature vector of time-ordered features representing characteristics of the measurements taken by the biochemical analysis system 1. Such a feature vector may be derived as described in detail in WO-2013/121224 to which reference is made and which is incorporated herein by reference. In that case, step C4 or D4 comprises the process shown in FIG. 15 which is performed as follows.

In step C4c-1, the chunk of measurements 63, which in this case is taken from the series of raw measurements 11, is analysed to derive a feature vector 66 of time-ordered features representing characteristics of the measurements.

In step C4c-2, the feature vector 66 is compared with the reference data 50 to derive the measure of similarity 65. The comparison may be performed using the methods described in detail in WO-2013/121224.

In a fourth example, the reference data 50 represents a reference model 70. In that case, step C4 or D4 comprises the process shown in FIG. 16 which comprises step C4d of fitting the model to the series of the chunk of measurements 63 to provide the measure of similarity 65 as the fit of the reference model 70 to the chunk of measurements 63. The chunk of measurements 63 may be the series of raw measurements 11 or the series of measurements 12.

Step C4d may be performed as follows.

The reference model 70 is a model of the reference sequence of polymer units in the biochemical analysis system 1. The reference model 70 treats the measurements as observations of a reference series of k-mer states corresponding to the reference sequence of polymer units. The k-mer states of the reference model 70 may model the actual k-mers on which the measurements depend, although mathematically this is not necessary and so the k-mer states may be an abstraction of the actual k-mers. Thus, the different types of k-mer states may correspond to the different types of k-mers that exist in the reference sequence of polymer units.

The reference model 70 may be considered as an adaption of the general model 60 of the type described above and in WO-2013/041878, to model the measurements that are obtained specifically when the reference sequence is measured. Thus, reference model 70 treats the measurements as observations of a reference series of k-mer states 73 corresponding to the reference sequence of polymer units. As such, the reference model 70 has the same form as the general model 60, in particular comprising transition weightings 71 and emission weightings 72 as will now be described.

The transition weightings 71 represent transitions between the k-mer states 73 of the reference series. Those k-mer states 73 correspond to the reference sequence of polymer units. Thus, successive k-mer states 73 in the reference series corresponds to a successive overlapping groups of k polymer units. As such there is an intrinsic mapping between the k-mer states 73 of the reference series and the polymer units of the reference sequence. Similarly, each k-mer states 73 is of a type corresponding to the combination of the different types of each polymer unit in the group of k polymer units.

Figure 17:
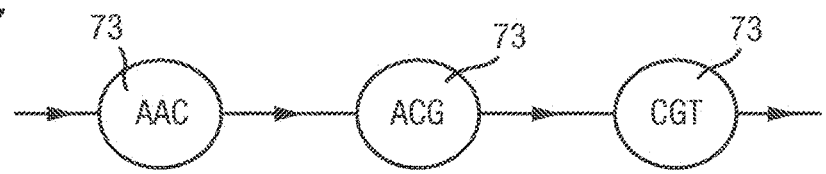
FIG. 17 is a state diagram of an example of a reference series of k-mer states.

This is illustrated with reference to the state diagram of FIG. 17 which shows an example of three successive k-mer states 73 in the reference series of estimated k-mer states 73. In this example, k is three and the reference sequence of polymer units includes successive polymer units labelled A, A, C, G, T. (although of course those specific types of the k-mer states 73 are not limitative). Accordingly, the successive k-mer states 73 of the reference series corresponding to those polymer units are of types AAC, ACG, CGT which correspond to a measured sequence of polymer units AACGT.

Figure 18:
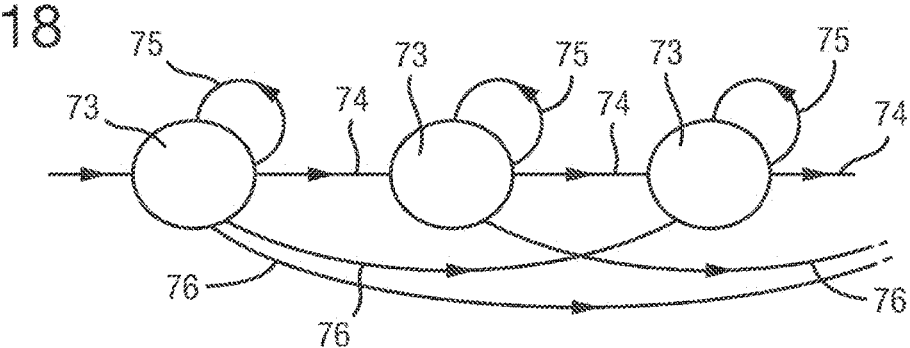
FIG. 18 is a state diagram of a reference series of k-mer states illustrating possible types of transition between the k-mer states.

The state diagram of FIG. 18 illustrates transitions between the k-mer states 73 of the reference series, as represented by the transition weightings 71. In this example, states may only forwards progress through the k-mer states 73 of the reference series is allowed (although in general backwards progression could additionally be allowed). Three different types of transition 74, 75 and 76 are illustrated as follows.

From each given k-mer state 73 in the reference series, a transition 74 to the next k-mer state 73 is allowed. This models the likelihood of successive measurements in the series of measurements 12 being taken from successive k-mers of the reference sequence of polymer units. In the case that the chunk of measurements 63 are pre-processed to identify successive groups of measurements and to derive a series of processed measurements for further analysis, consisting of a predetermined number of measurements in respect of each identified group, the transition weightings 71 represent this transition 74 as having a relatively high likelihood.

From each given k-mer state 73 in the reference series, a transition 75 to the same k-mer state is allowed. This models the likelihood of successive measurements in the series of measurements 12 being taken from the same k-mers of the reference sequence of polymer units. This may be referred to as a "stay". In the case that the chunk of measurements 63 are pre-processed to identify successive groups of measurements and to derive a series of processed measurements, consisting of a predetermined number of measurements in respect of each identified group, the transition weightings 71 represent this transition 75 as having a relatively low likelihood compared to the transition 74.

From each given k-mer state 73 in the reference series, a transition 76 to the subsequent k-mer states 73 beyond the next k-mer state 73 is allowed. This models the likelihood of no measurement being taken from the next k-mer state, so that successive measurements in the series of measurements 12 being taken from k-mers of the reference sequence of polymer units that are separated. This may be referred to as a "skip". In the case that the chunk of measurements 63 are pre-processed to identify successive groups of measurements and to derive a series of processed measurements, consisting of a predetermined number of measurements in respect of each identified group, the transition weightings 71 represent this transition 76 as having a relatively low likelihood compared to the transition 74.

The level of the transition weightings 71 representing the transitions 75 and 76 for skips and stays relative to the level of the transition weightings 71 representing the transitions 74 may be derived in the same manner as the transition weightings 61 for skips and stays in the general model 31, as described above.

In the alternative that the chunk of measurements 63 are not pre-processed to identify successive groups of measurements and to derive a series of processed measurements, so that the further analysis is performed on the chunk of measurements 63 themselves, then the transition weightings 71 are similar but are adapted to increase the likelihood of the transition 75 representing a skip to represent the likelihood of successive measurements being taken from the same k-mer. The level of the transition weightings 71 for the transition 75 are dependent on the number of measurements expected to be taken from any given k-mer and may be determined by experiment for the particular biochemical analysis system 1 that is used.

Emission weightings 72 are provided in respect of each k-mer state. The emission weightings 72 are weightings for different measurements being observed when the k-mer state is observed. The emission weightings 72 are therefore dependent on the type of the k-mer state in question. In particular, the emission weightings 72 for a k-mer state of any given type are the same as the emission weightings 62 for that type of k-mer state in the general model 60 as described above.

Step C4d of fitting the model to the series of the chunk of measurements 63 to provide the measure of similarity 65 as the fit of the reference model 70 to the chunk of measurements 63 is performed using the same techniques as described above with reference to FIG. 13, except that the reference model 70 replaces the general model 60.

As a result of the form of the reference model 70, in particular the representation of transitions between the reference series of k-mer states 73, the application of the model intrinsically derives an estimate of an alignment mapping between the chunk of measurements 63 and the reference series of k-mer states 73. This may be understood as follows. As the general model 60 represents transitions between the possible types of k-mer state, the application of the model provides estimates of the type of k-mer state from which each measurement is observed. As the reference model 70 represents transitions between the reference series of k-mer states 73, the application of the reference model 70 instead estimates the k-mer state 73 of the reference sequence from which each measurement is observed, which is an alignment mapping between the series of measurements and the reference series of k-mer states 73.

In addition, the algorithm derives a score for the accuracy of the alignment mapping, for example representing the likelihood that the estimate of the alignment mapping is correct, for example because the algorithm derives the alignment mapping based on such a score for different paths through the model. Thus, this score for the accuracy of the alignment mapping is therefore the measure of similarity 65

As an example in the case that the reference model 70 is an HMM and the analytical technique applied is the Viterbi algorithm as described above, then the score is simply the likelihood predicted by the reference model 70 associated with the derived estimate of the alignment mapping.

As another example in the in the case that the general model 60 is an HMM, the analytical technique may be of the type disclosed in Fariselli et al., as described above. This again derives a score that is the measure of similarity 65.

The reference model 70 may be generated from the reference sequence of polymer units or from measurements taken from the reference sequence of polymer units, as follows.

Figure 19:
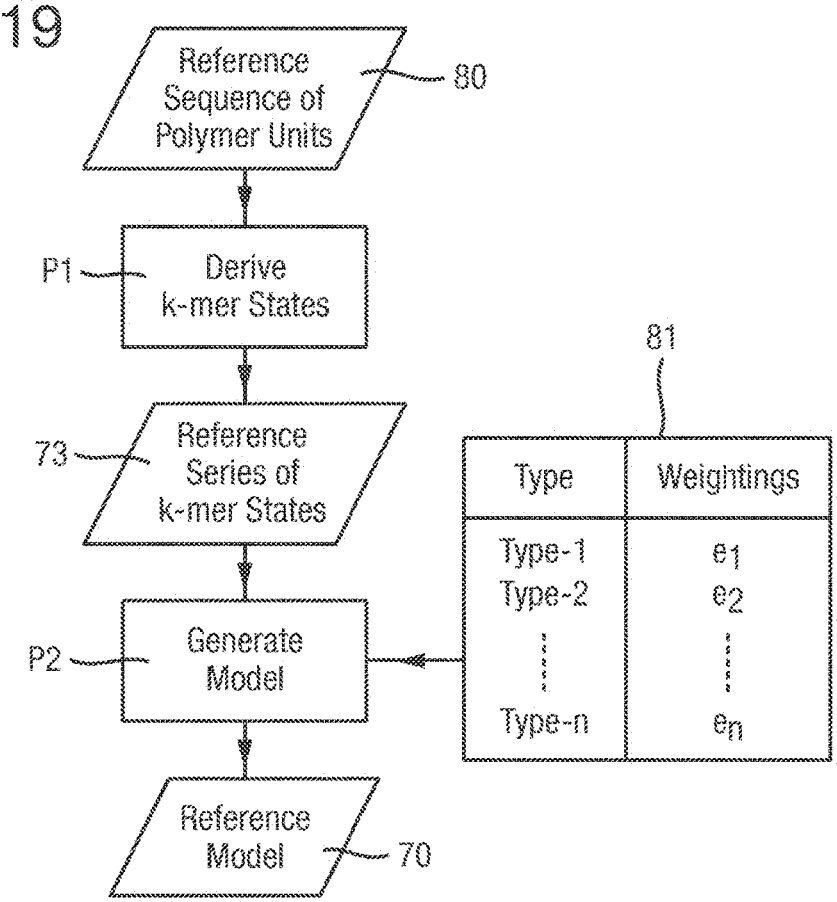
FIG. 19 is a flow chart of a first process for generating a reference model.

The reference model 70 may be generated from a reference sequence of polymer units 80 by the process shown in FIG. 19, as follows. This is useful in applications where the reference sequence is known, for example from a library or from earlier experiments. The input data representing the reference sequence of polymer units 80 may already be stored in the data processor 5 or may be input thereto.

This process uses stored emission weightings 81 which comprise the emission weightings e1 to en in respect of a set of possible types of k-mer state type-1 to type-n. Advantageously, this allows generation of the reference model for any reference sequence of polymer units 80, based solely on the stored emission weightings 81 for the possible types of k-mer state.

The process is performed as follows.

In step P1, the reference sequence of polymer units 80 is received and a reference sequence of k-mer states 73 is generated therefrom. This is a straightforward process of establishing, for each k-mer state 73 in the reference sequence, the type of that k-mer state 73 based on the combination of types of polymer unit 80 to which that k-mer state 73 corresponds.

In step P2, the reference model is generated, as follows.

The transition weightings 71 are derived for transitions between the reference series of k-mer states 73 derived in step P1. The transition weightings 71 take the form described above, defined with respect to the reference series of k-mer states 73.

The emission weightings 72 are derived for each k-mer state 73 in the series of k-mer states 73 derived in step P1, by selecting the stored emission weightings 81 according to the type of the k-mer state 73. For example, if a given k-mer state 73 is of type type-4, then the emission weightings e4 are selected.

Figure 20:
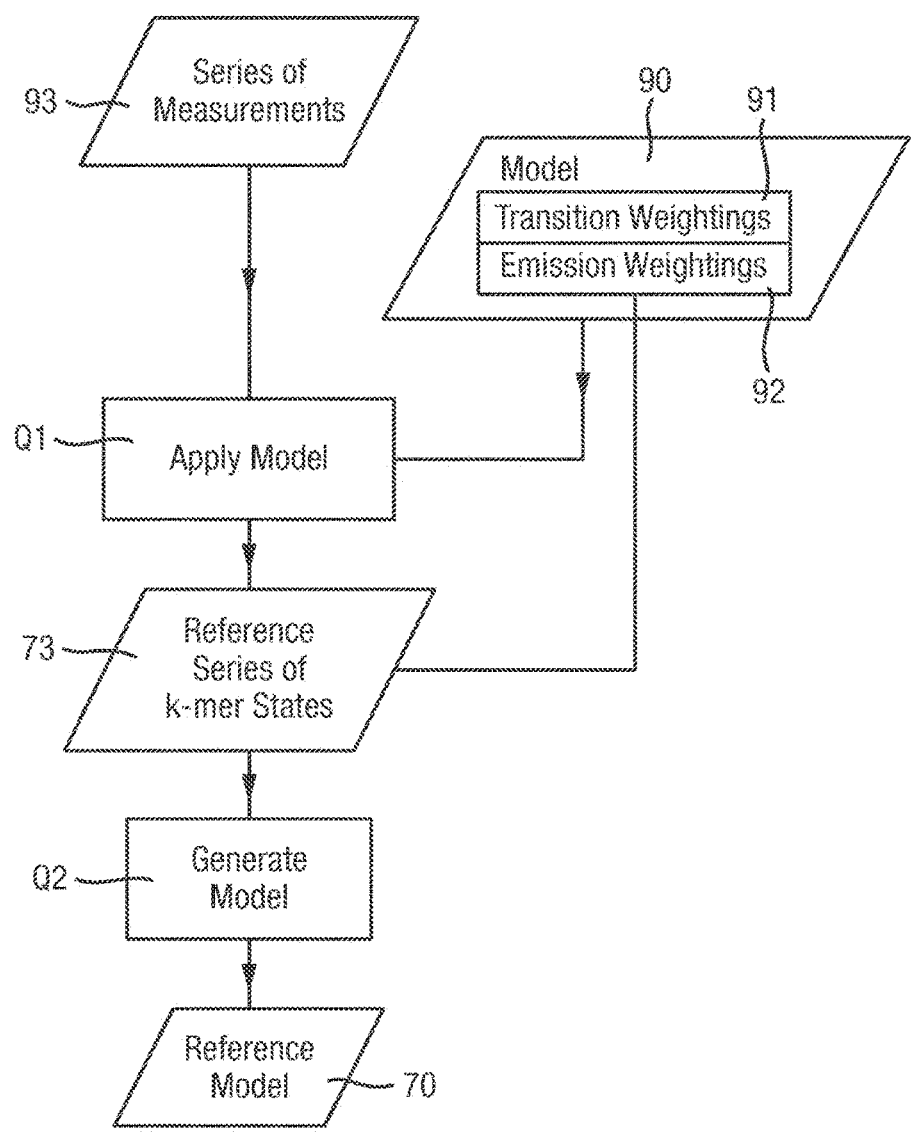
FIG. 20 is a flow chart of a second process for generating a reference model.

The reference model 70 may be generated from a series of reference measurements 93 taken from the reference sequence of polymer units by the process shown in FIG. 20, as follows. This is useful, for example, in applications where the reference sequence of polymer units is measured contemporaneously with the target polymer. In particular, in this example there is no requirement that the identity of the polymer units in the reference sequence are themselves known. The series of reference measurements 93 may be taken from the polymer that comprises the reference sequence of polymer units by the biochemical analysis system 1.

This process uses a further model 90 that treats the series of reference measurements as observations of a further series of k-mer states of different possible types. This further model 90 is a model of the biochemical analysis system 1 used to take the series of reference measurements 93 and may be identical to the general model 60 described above, for example of the type disclosed in WO-2013/041878. Thus, the further model comprises transition weightings 91 in respect of each transition between successive k-mer states in the further series of k-mer states, that are transition weightings 91 for possible transitions between the possible types of the k-mer states; and emission weightings 92 in respect of each type of k-mer state, being emission weightings 92 for different measurements being observed when the k-mer state is of that type.

The process is performed as follows.

In step Q1, the further model 90 is applied to the series of reference measurements 93 to estimate the reference series of k-mer states 73 as a series of discrete estimated k-mer states. This may be done using the techniques described above.

In step Q2, the reference model 70 is generated, as follows.

The transition weightings 71 are derived for transitions between the reference series of k-mer states 73 derived in step Q1. The transition weightings 71 take the form described above, defined with respect to the reference series of k-mer states 73.

The emission weightings 72 are derived for each k-mer state 73 in the series of k-mer states 73 derived in step Q1, by selecting the emission weightings from the weightings of the further model 50 according to the type of the k-mer state 73. Thus, the emission weightings for each type of k-mer state 73 in the reference model are the same as the emission weightings for that type of k-mer state 73 in the further model 50.

Examples of various applications of the method shown in FIG. 7, and more generally in accordance with the first aspect of the present invention, will now be described, explaining the nature of the reference sequence of polymer units, the basis of the decision in step C4 and an indication of possible time-savings. In the following examples, the polymers are polynucleotides and an assumption has been made that measurement of the first 250 nucleotides followed by comparison to a reference sequence will be enough to determine (a) whether it relates to that reference sequence or not and (b) its location with respect to the overall sequence. However it may be more or less than this number. The number of polymer units required to make a determination will not necessarily be fixed. Typically measurements will be continually carried out on a continual basis until such a determination can be made.

For each of the types of application, there might be a slightly different use of the method shown in FIG. 7. A mixture of the types of application might also be used. The analysis performed in step C3 and/or the basis of the decision in step C4 might also be adjusted dynamically as the run proceeds. For example, there might be no decision logic applied initially, then logic is used later into the run when enough data has built up to make decisions. Alternatively, the decision logic may change during a run.

In a first type of application, the reference sequence of polymer units from which the reference data 50 is derived is an unwanted sequence, and in step C4 a decision to reject the polymer is made to responsive to the measure of similarity indicating that the partially translocated polymer is the unwanted sequence.

This first type of application has multiple potential uses. For example, such an application may be used to sequence incomplete portions of the genome of an organism. If the genome of an organism has been partially defined, but the sequence is incomplete, the incomplete portions of the sequence can be determined using the method of the invention. In such an embodiment, the reference sequence may be the sequence of the complete portions of the genome. The polymers may be fragments of a polynucleotide from the organism. If the measure of similarity indicates that the polymer is the reference sequence (i.e. the sequence of the already defined portions of the genome), the polymer is rejected and a new polymer can be received by the nanopore. This can be repeated until a polymer which is not similar to the reference sequence has partially translocated through the nanopore, such a polymer will correspond to a previously undefined portion of the genome and can be retained in the nanopore and sequenced in its entirety. This method allows for rapid sequencing of the undefined portions of the genome.

The first type of application may also be beneficially used to sequence polymers from a sample of polymers comprising human DNA. The sequencing of human DNA has ethical issues associated with it. Thus, it is useful to be able to sequence a sample of polymers and to disregard sequences of human DNA (for example identification of bacteria in a sample extracted from a human patient). In this case the reference sequence (the unwanted sequence) may be the human genome. Any polymers having a measure of similarity indicating that they correspond to part of the human genome may be rejected, whilst polymers having a measure of similarity indicating that they do not correspond to the human genome may be retained in the nanopore and sequenced fully. Thus, this is an example of a method where the measure of similarity indicates similarity with a portion of the reference sequence. In this application, the method avoids sequencing the human DNA, but allow for the bacterial DNA to be sequenced. If the bacterium is in a sample from human intestines, we assume that the bacterial DNA (which is the DNA that we want to sequence, or the "on target" DNA) is approximately 5% of the DNA and 95% of the DNA in the sample is the human DNA ("off-target DNA"). If we assume that the sequence of around 250 bp (base-pairs) of each fragment will be sufficient to provide the required measure of similarity, and that the polymers can translocate through the pores at a rate of 25 bases per second then a polymer which is not the target DNA i.e. DNA similar to the human DNA reference sequence (the "off-target" polymer) will translocate through the nanopore for approximately 10 seconds before it is ejected. Thus the relative amount of time in which the nanopores contain off-target polymer can be considered to be 95%×10=9.5. On the other hand, assuming that the DNA is fragmented into 10 Kb fragments, the amount of time it takes to sequence one fragment of on-target DNA will be 10,000/25 which is 400 seconds. Thus the relative amount of time in which the nanopores contain on-target polymer can be considered to be 5%×400 which is 20 seconds. So the proportion of time in which the nanopores contain on-target strands can be considered to be time in which the nanopores contain on-target strands/time in which the nanopores contain off-target strands+time in which the nanopores contain on-target strands which is 20/29.5. On the other hand if the off-target strands had to be sequenced in their entirety the relative amount of time in which the nanopores contain off-target strands would be 95%×400 which is 380 and so the proportion of time which the nanopores contain on-target strands can be considered to be 20/380. This represents an efficiency of around 13.6 times.

The first type of application may also be beneficially used to sequence contaminants in a sample. In such an embodiment the reference sequence would be the sequence of the components known to be present in the sample. For example, this could be used to detect contaminants in a food product such as a meat product like a beef product. In this case the reference sequence would be the sequence of polynucleotides from the organism from which the food product is derived (for example the genome of that organism). The reference sequence may be the sequence of the genome of a cow. Any polymers in the sample having a measure of similarly indicating that they correspond to the cow genome may be rejected, whilst polymers having a measure of similarity indicating that they do not correspond to the cow genome may be retained in the nanopore and sequenced fully. This would allow the nature of the contaminant to be defined quickly and simply without the need to know the nature of the contaminant. This is advantageous over prior art methods such as quantitative PCR which required knowledge of the suspected contaminant. Assuming that 99% of the DNA is off-target (meat DNA) and 1% of the DNA is on-target (for example the contaminant) then the method of the invention would be around 29 times more efficient than if the nanopore was not able to eject unwanted polymers.

In a second type of application, the reference sequence of polymer units from which the reference data 50 is derived is a target, and in step C4 a decision to reject the polymer is made to responsive to the measure of similarity indicating that the partially translocated polymer is not the target.

This second type of application may be beneficially used to sequence a gene of interest from a sample of DNA. In such an application the reference sequence is a target which may be a portion of a polynucleotide such as a gene of interest, and the polymers may comprise fragments of polynucleotides such as DNA from the sample. Any polymers in the sample having a measure of similarity indicating that they are not similar to the target (gene of interest) may be rejected. The remaining polymers may be retained and sequenced. This allows for rapid sequencing of a gene of interest and is advantageous over prior art methods which require isolating the target gene of interest before sequencing it (for example by hybridisation of the gene of interest to probes attached to a solid surface). Such isolation techniques are time consuming and are not required when using the method of the invention. One example of such an application would be the sequencing of the human genome. The human genome contains 50 Mb (Mega-bases) of coding sequence. It would be ideal to be able to sequence that 50 Mb and not the remaining 3,000 Mb. Thus, the amount of DNA which is "off target" (which should be rejected) is 3,000 Mb. The DNA will be fragmented into fragments approximately 10 Kb in length, and therefore 3,000 Mb will represent approximately 300,000 fragments. Assuming that the sequence of around 250 bp of each fragment will be sufficient to provide the required measure of similarity, and that the polymers can translocate through the pores at a rate of 25 bases per second then a polymer which is not similar to the target polymer ("off-target" human DNA) will translocate through the nanopore for approximately 10 seconds before it is ejected. Since there are 300,000 off-target fragments, then the off-target fragments will be retained within the pores for around 3,000,000 seconds per nanopore (number of fragments multiplied by the time each fragment remains in the pore—approximately 10 seconds). The remaining 50 Mb which is similar to the target polymer ("on-target") will take 2,000 seconds (at 25 bases per second the time taken will equal 50,000,000/25 or 2,000,000 seconds). The total time to sequence the described 50 Mb of the target polymer is the sum of the amount of time taken to sequence off-target polymer and the amount of time taken to sequence on-target polymer, which is 3,000,000+2,000,000 or 5,000,000 seconds per nanopore. On the other hand if the entirety of each of the 300,000 off-target fragments was sequenced, then this would take 3,000,000,000/25 (3,000 Mb sequenced at a rate of 25 base pair per second)+2,000, 000 (the time taken to sequence the on-target sequence) which is 122,000,000 seconds per pore (over 50 times longer) to sequence the genome once.

This second type of application may also be beneficially used to identify whether bacteria in a sample (for example from a hospitalised patient) are antibiotic resistant. Here the reference sequence will be a target which may be a polynucleotide corresponding to a particular antibiotic resistance gene. Any polymers in the sample having a measure of similarity indicating that they are not similar to the target antibiotic resistance gene may be rejected. If no polymers are detected having a measure of similarity indicating that they are similar to the antibiotic resistance gene, this would indicate that the bacterium is missing the particular antibiotic resistance gene. Alternatively, if polymers are detected that do have a measure of similarity indicating that they are similar to the antibiotic resistance gene, these may be retained and sequenced, and the sequence used to determine whether the antibiotic resistance gene is functional. In such a case the off-target polymer (genome of the bacterium) will be around 5000 kb and the on-target polymer (region of interest) will be around 5 kb. Making the same assumptions as described above, means that the method of the invention would sequence the DNA approximately 40 times faster than if the nanopore was not able to eject unwanted polymers.

This second type of application may also be beneficially used to sequence total bacterial mRNA. In this case, it is desirable to be able to sequence mRNA but to be able to disregard sequences of rRNA or tRNA. Here the reference sequence may be a target sequence such as an annotated version of the bacterial genome. The polymers may comprise RNA from a sample of the bacterium. Any polymers in the sample having a measure of similarity indicating that they are not similar to the target bacterial genome will relate to rRNA or tRNA and can be rejected. The remaining polymers will correspond to mRNA and can be sequenced to provide the sequence of the total bacterial mRNA. In this case the on target polymer would be the mRNA (which is approximately 5% of the total RNA) and the off-target polymer would be the tRNA and the rRNA which is approximately 95% of the total RNA. Using the same assumptions as those defined above, we would expect an increase in sequencing efficiency of around 8.4 times.

This second type of application may also be beneficially used to identify a bacterial strain, for phenotyping or for SNP (single-nucleotide polymorphism) detection, where the strain of the bacterium is not known. For example, in this case the polymers may be fragments of polynucleotides from a bacterial sample. Initially no polymers are rejected (no reference sequence is used) and any polymer which has partially translocated through the pores is sequenced, but when sufficient sequence information has been obtained to allow the user to determine the strain of the bacteria, then a reference sequence is selected. The reference sequence will correspond to a target region of interest and will depend on the species of bacterium which has been defined. Once the reference sequence has been defined any polymers which partially translocate through the pores and have a measure of similarity indicating that they are similar to the reference sequence (the target portion of interest) are be retained and sequenced fully, whilst other polymers may be rejected. This will allow detection of phenotype or the presence of SNPs.

Similarly this second type of application could be useful in the phenotyping of cancer. In this application the polymers may be fragments of polynucleotides obtained from a cancer patient. Initially the reference sequence may be target sequences. These target sequences may be sequences of polynucleotides such as genes associated with different classes of cancers. Any polymers having a measure of similarity to these target sequences will be retained and other polymers rejected. However, once the class of cancer has been identified the reference sequence can be refined such that the reference sequence now comprises targets having sequences of polynucleotides associated with sub-classes of cancer.

In a third type of application, the reference sequence of polymer units from which the reference data 50 is derived an already measured sequence of polymer units, and in step C4 a decision to reject the polymer is made to responsive to the measure of similarity indicating that the partially translocated polymer is already measured sequence of polymer units.

Such a type of application may be used to enable accurate sequencing of a genome. The determination of the sequence of a genome requires that sequences of multiple strands of DNA is performed, and for accuracy, a consensus sequences for that portion of DNA should be determined. Thus polymers corresponding to the same portion of that sequence should be sequenced enough times to be able to define an accurate consensus sequence. For this reason, the method of the invention may be used to quickly and accurately sequence a genome. For example, the polymers may comprise DNA from a sample of the DNA of the organism for which the genome is to be defined. The reference sequence is a portion of that DNA for which sufficient measurements have already been taken (in this case for which sufficient sequence data has been obtained to provide an accurate consensus sequence). Initially no sequences are rejected. However, once it has been calculated that sufficient sequence data for a portion of the genome has been obtained to allow for calculation of an accurate consensus sequence, that consensus sequence becomes the target (reference sequence). Any polymers which partially translocate through the pores and have a measure of similarity indicating that they are similar to the reference sequence (portion of DNA for which an accurate consensus sequence has already been defined) can be rejected, freeing up the nanopores to sequence other portions of the genome for which sufficient information has not already been collected.

In a fourth type of application, the reference sequence of polymer units from which the reference data 50 is derived comprises plural targets, and in step C4 a decision to reject the polymer is made to responsive to the measure of similarity indicating that the partially translocated polymer is one of the targets.

This is a counting method that can be used to quantify the proportion of each target polymer in a sample of target polymers. For example, the targets may represent different polymers. When a polymer partially translocates through the nanopore, any polymer which has a measure of similarity indicating that they are similar to the reference sequence can be assigned to one "bucket" and the number of polymers detected belonging to each "bucket" can be quantified. In such an embodiment the polymer will be rejected once sufficient information has been obtained about the polymer to determine whether it has a measure of similarity indicating that it is similar to one of the reference sequences. An example of the use of such a technique is the quantification of a contaminant. For example the polymers may be a sample of a food product such as a beef product. In this case the reference sequence may comprise a target having a sequence found in cow DNA and a target having a sequence found in horse DNA. The proportion of polymers which are similar to the cow DNA target and the proportion of polymer whish are similar to the horse DNA can be calculated using this method, and this will indicate the level of contamination of a beef product with horse meat.

Similarly if the reference sequence used comprises targets having sequences found in different bacteria, this technique can be used to determine the proportion of different bacteria present in a sample, such as a sample from an infected patient.

Figure 16:
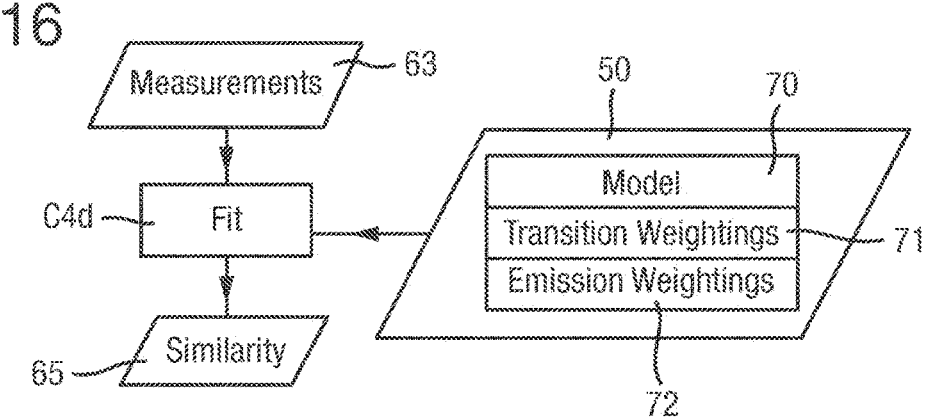

The method shown in FIG. 16 results in generation of an alignment mapping. This method may be applied more generally as follows.

Figure 21:
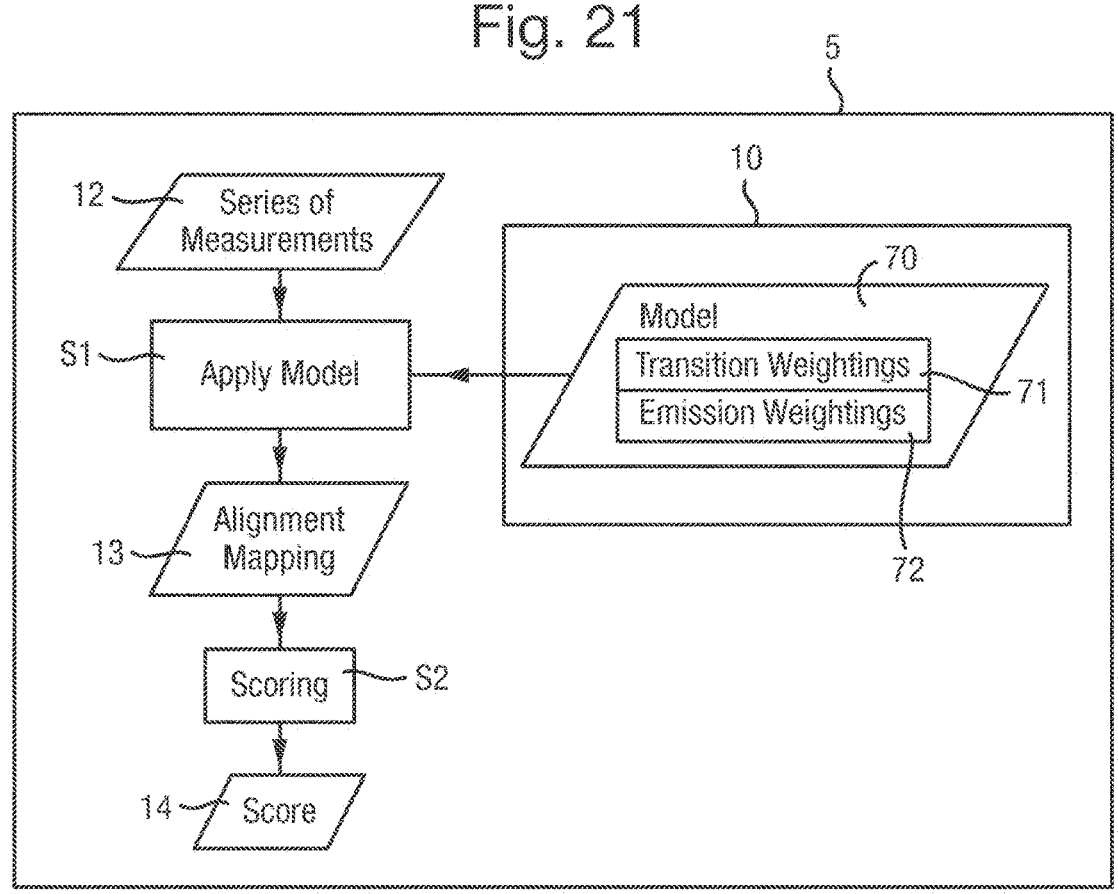
FIG. 21 is a flowchart of a method of estimating an alignment mapping.

FIG. 21 shows a method of estimating an alignment mapping between (a) a series of measurements of a polymer comprising polymer units, and (b) a reference sequence of polymer units. The method is performed as follows.

As shown in FIG. 21, the input to the method may be a series of measurements 12 derived by taking a series of raw measurements from a sequence of polymer units by the biochemical analysis system 1 and subjecting them to pre-processing as described above. As an alternative, the input to the method may be a series of raw measurements 11.

The method uses the reference model 70 of the reference sequence of polymer units, the reference model 70 being stored in the memory 10 of the data processor 5. The reference model 70 takes the same form as described above, treating the measurements as observations of a reference series of k-mer states corresponding to the reference sequence of polymer units.

The reference model 70 is used in alignment step S1. In particular, in alignment step S1, the reference model 70 is applied to the series of measurements 12. Alignment step S1 is performed in the same manner as step C4d above. In other words, alignment step S1 is performed by fitting the model to the series of the chunk of measurements 63 to provide the measure of similarity 65 as the fit of the reference model 70 to the chunk of measurements 63 is performed using the same techniques as described above with reference to FIG. 13, except that the reference model 70 replaces the general model 60.

As a result of the form of the reference model 70, in particular the representation of transitions between the reference series of k-mer states 73, the application of the model intrinsically derives an estimate 13 of an alignment mapping between the series of measurements and the reference series of k-mer states 73. This may be understood as follows. As the general model 60 represents transitions between the possible types of k-mer state, the application of the model provides estimates of the type of k-mer state from which each measurement is observed, i.e. the initial series of estimates of k-mer states 34 and the discrete estimated k-mer states 35 which each estimate the type of the k-mer state from which each measurement is observed. As the reference model 70 represents transitions between the reference series of k-mer states 73, the application of the reference model 70 instead estimates the k-mer state 73 of the reference sequence from which each measurement is observed, which is an alignment mapping between the series of measurements and the reference series of k-mer states 73.

As there is an intrinsic mapping between the k-mer states 73 of the reference series and the polymer units of the reference sequence, the alignment mapping between the series of measurements and the reference series of k-mer states 73 also provides an alignment mapping between the series of measurements and the reference sequence of polymer units.

Figure 22:
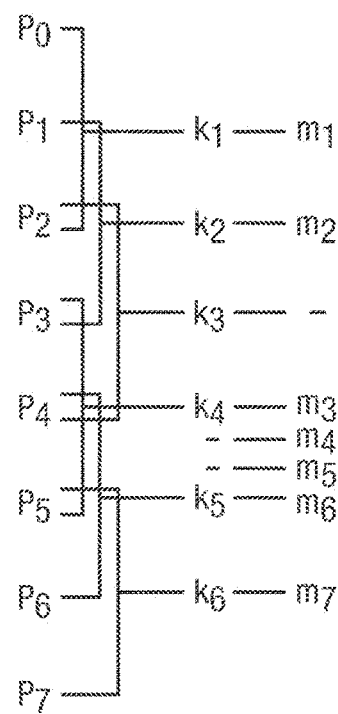
FIG. 22 is a diagram of an alignment mapping.

FIG. 22 illustrates an example of an alignment mapping to illustrate its nature. In particular, FIG. 22 shows an alignment mapping between polymer units p0 to p7 of the reference sequence, k-mer states k1 to k6 of the reference series and measurements m1 to m7. By way of illustration in this example k is three. The horizontal lines indicate an alignment between a k-mer state and a measurement, or in the case of a dash an alignment to a gap in the other series. Thus, inherently the polymer units p0 to p7 of the reference sequence are aligned to k-mer states k1 to k6 of the reference series as illustrated. K-mer state k1 corresponds to, and is mapped to, polymer units p1 to p3 and so on. As to the mapping between k-mer states k1 to k6 of the reference series and measurements m1 to m7: k-mer state k1 is mapped to measurement m1, k-mer state k2 is mapped to measurement m2, k-mer state k3 is mapped to a gap in the series of measurements, k-mer state k4 is mapped to measurement m3, and measurements m4 and m5 are mapped to a gap in the series of k-mer states.

Depending on the method applied, the form of the estimate 13 of the alignment mapping may vary, as follows.

As noted above, the analytical technique applied in the alignment step S1 may take a variety of forms that are suitable for the form of the reference model 70. For example in the case that the reference model 70 is an HMM, the analytical technique may be a known algorithm for solving the HMM, for example the Forwards-Backwards algorithm or the Viterbi algorithm, which is well known in the art. Such algorithms in general avoid a brute force calculation of the likelihood of all possible paths through the sequence of states, and instead identify state sequences using a simplified method based on the likelihood.

With some techniques applied in the alignment step S1, the derived estimate 13 of the alignment mapping comprises, for each measurement 12 in the series, weightings in respect of different k-mer states 73 in the reference series of k-mer states 73. For example, such an alignment mapping may be represented by $M_{i,j}$ where the index i labels the measurements and the index j labels the k-mer states in the reference series, and so where there are K k-mer states the values $M_{i,1}$ to $M_{i,K}$ represents the weightings in for the i-th measurement in respect of each k-mer state 73 in the reference series of k-mer states 73. In this case, the estimate 13 does not represent a single k-mer state 73 as being mapped to each measurement, but instead provides weightings for different possible k-mer states 73 being so mapped to each measurement.

As an example in the case that the reference model 70 is an HMM, the derived estimate may be of this type when the analytical technique applied is the Forwards-Backwards algorithm as described above. In the Forwards-Backwards algorithm, the total likelihood of all sequences ending in a given k-mer state is calculated recursively in for forwards and backwards directions using the transition and emission weightings. These forwards and backwards probabilities are combined along with the total likelihood of the data to calculate the probability of each measurement being from a given k-mer state. This matrix of probabilities termed the posterior matrix is the estimate 13 of the alignment mapping.

In this case, in a subsequent scoring step S2 (which is optional), there is derived a score 14 representing the likelihood that the estimate 13 of the alignment mapping is correct. This may be derived from the estimate 13 of the alignment mapping itself using a straightforward probabilistic technique, or alternatively may be derived as an intrinsic part of alignment step S1

With other techniques applied in the alignment step S1, the derived estimate 13 of the alignment mapping comprises, for each measurement in he series, a discrete estimate of a k-mer state in the reference series of k-mer states. For example, such an alignment mapping may be represented by $M_i$ where the index i labels the measurements and $M_i$ can take the values 1 to K indicating the K k-mer states. In this case, the estimate 13 represents a single k-mer state 73 as being mapped to each measurement.

As an example in the case that the reference model 70 is an HMM, the derived estimate may be of this type when the analytical technique applied is the Viterbi algorithm as described above, wherein the analysis technique estimates the sequence of k-mers based on the likelihood predicted by the model of the series of measurements being produced by the reference series of k-mer states.

In this case that derived estimate 13 of the alignment mapping comprises discrete estimates of a k-mer state, the algorithm intrinsically derives the score 14 representing the likelihood that the estimate 13 of the alignment mapping is correct, because the algorithm derives the alignment mapping based on such a score for different paths through the model. Thus, in this case a separate scoring step S2 is not performed. As an example in the case that the reference model 70 is an HMM and the analytical technique applied is the Viterbi algorithm as described above, then the score is simply the likelihood predicted by the model associated with the derived estimate 13 of the alignment mapping.

The method shown in FIG. 21 has a wide range of applications in which it is desirable to estimate an alignment mapping between a series of measurements of a polymer and a reference sequence of polymer units and/or a score indicating the likelihood of the alignment mapping being accurate. Such estimation of an alignment mapping may be used in a variety of applications such as comparison to a reference to provide identification or detection of the presence, absence or extent of a polymer in a sample, for example to provide a diagnosis. The potential range of specific applications is vast and could be applied to the detection of any analyte having a DNA sequence.

The above example refers to a single reference model 70. In many applications, multiple reference models 70 may be used. The method shown in FIG. 21 may be applied using each reference model 70, or one of the reference models 70 may be selected. The selection may be made based on various criteria, depending on the application. For example, the reference models 70 may be applicable to different types of sensor device 2 (e.g. different nanopores) and/or ambient conditions, in which case the selection of the reference model 8 is based on the type of sensor device 2 actually used and/or the actual ambient conditions. In another example, the selection may be made based on an analyte to be detected, for example whether particularly G/C rich or whether the experiment is to determine particular epigenetic information.

Thus, according to the fourth aspect of the present invention, there is provided a method of estimating an alignment mapping between (a) a series of measurements of a polymer comprising polymer units, wherein the measurements are dependent on a k-mer, being k polymer units of the polymer, where k is an integer, and (b) a reference sequence of polymer units;

the method using a reference model that treats the measurements as observations of a reference series of k-mer states corresponding to the reference sequence of polymer units, wherein the reference model comprises:

transition weightings for transitions between the k-mer states in the reference series of k-mer states; and in respect of each k-mer state, emission weightings for different measurements being observed when the k-mer state is observed; and the method comprising applying the reference model to the series of measurements to derive an estimate of an alignment mapping between the series of measurements and the reference series of k-mer states corresponding to the reference sequence of polymer units.

The following features may optionally be applied in the fourth aspect of the present invention, in any combination:

The estimate of the alignment mapping may comprise, for each measurement in the series, a discrete estimate of a mapped k-mer state in the reference series of k-mer states.

The estimate of the alignment mapping may comprise, for each measurement in the series, weightings in respect of different mapped k-mer states in the reference series of k-mer states.

The method may further comprise deriving a score representing the likelihood that the estimate of the alignment mapping is correct.

The method may further comprise generating the reference model from the reference sequence of polymer units using stored emission weightings in respect of a set of possible types of k-mer state, by a process comprising:

deriving the series of k-mer states corresponding to received reference sequence of polymer units;

generating the reference model by generating the transition weightings for transitions between the k-mer states in the derived series of k-mer states, and by selecting emission weightings for each k-mer state in the derived series from the stored emission weightings according to the type of the k-mer state.

The method may further comprise generating the reference model from a series of reference measurements of a polymer comprising the reference sequence of polymer units.

The step of generating the reference model may uses a further model that treats the series of reference measurements as observations of a further series of k-mer states of different possible types, wherein the further model comprises:

in respect of each transition between successive k-mer states in the further series of k-mer states, transition weightings for possible transitions between the possible types of the k-mer states; and in respect of each type of k-mer state, emission weightings for different measurements being observed when the k-mer state is of that type, the step of generating the reference model comprising:

generating the reference series of estimates of k-mer states by applying the further model to the series of reference measurements; and generating the reference model by generating transition weightings for transitions between the k-mer states in the generated reference series of estimates of k-mer states and by selecting emission weightings for each k-mer state in the generated reference series of estimates from the weightings of the further model according to the type of the k-mer state.

The reference model may be pre-stored.

One or both of the transition weightings and the emission weightings may be probabilities.

The model may be a Hidden Markov Model.

The integer k may be a plural integer.

The measurements may be measurements taken during translocation of said polymer through a nanopore.

The translocation of said polymer through a nanopore may be performed in a ratcheted manner.

The nanopore may be a biological pore.

The polymer may be a polynucleotide, and the polymer units may be nucleotides.

A single measurement may be dependent on a k-mer, or a predetermined plural number of measurements of different natures may be dependent on the same k-mer.

The measurements may comprise one or more of current measurements, impedance measurements, tunneling measurements, field effect transistor measurements and optical measurements.

The reference model may be stored in a memory.

The method may further comprise, before the step of applying the reference model to the series of measurements, deriving said series of measurements by:

receiving a series of raw measurements from the polymer, in which series of raw measurements groups of plural raw measurements are dependent on the same k-mer, without a priori knowledge of the number of measurements in the group, and processing the series of raw measurements to identify successive groups of measurements and in respect of each identified group deriving a single measurement or plural measurements of different types to form said series of measurements.

The method may further comprise taking said series of raw measurements from the polymer.

In each of said plural series of measurements, groups of plural measurements may be dependent on the same k-mer, without a priori knowledge of number of measurements in the group.

The method may further comprise taking said series of measurements from the polymer.

Sequence Listing
Seq ID 1: MS-(B1)8 = MS-(D90N/D91N/D93N/D118R/D134R/E139K)8
ATGGGTCTGGATAATGAACTGAGCCTGGTGGACGGTCAAGATCGTACCCTGACG

GTGCAACAATGGGATACCTTTCTGAATGGCGTTTTTCCGCTGGATCGTAATCGCC

TGACCCGTGAATGGTTTCATTCCGGTCGCGCAAAATATATCGTCGCAGGCCCGGG

TGCTGACGAATTCGAAGGCACGCTGGAACTGGGTTATCAGATTGGCTTTCCGTGG

TCACTGGGCGTTGGTATCAACTTCTCGTACACCACGCCGAATATTCTGATCAACA

ATGGTAACATTACCGCACCGCCGTTTGGCCTGAACAGCGTGATTACGCCGAACCT

GTTTCCGGGTGTTAGCATCTCTGCCCGTCTGGGCAATGGTCCGGGCATTCAAGAA

GTGGCAACCTTTAGTGTGCGCGTTTCCGGCGCTAAAGGCGGTGTCGCGGTGTCTA

ACGCCCACGGTACCGTTACGGGCGCGGCCGGCGGTGTCCTGCTGCGTCCGTTCGC

GCGCCTGATTGCCTCTACCGGCGACAGCGTTACGACCTATGGCGAACCGTGGAA

TATGAACTAA

Seq ID 2: MS -(B1)8 = MS-(D90N/D91N/D93N/D118R/D134R/E139K)8
GLDNELSLVDGQDRTLTVQQWDTFLNGVFPLDRNRLTREWFHSGRAKYIVAGPGA

DEFEGTLELGYQIGFPWSLGVGINFSYTTPNILINNGNITAPPFGLNSVITPNLFPGVSIS

ARLGNGPGIQEVATFSVRVSGAKGGVAVSNAHGTVTGAAGGVLLRPFARLIASTGD

SVTTYGEPWNMN

Seq ID 3: MS-(B2)8 = MS-(L88N/D90N/D91N/D93N/D118R/D134R/
E139K)8
ATGGGTCTGGATAATGAACTGAGCCTGGTGGACGGTCAAGATCGTACCCTGACG

GTGCAACAATGGGATACCTTTCTGAATGGCGTTTTTCCGCTGGATCGTAATCGCC

TGACCCGTGAATGGTTTCATTCCGGTCGCGCAAAATATATCGTCGCAGGCCCGGG

TGCTGACGAATTCGAAGGCACGCTGGAACTGGGTTATCAGATTGGCTTTCCGTGG

TCACTGGGCGTTGGTATCAACTTCTCGTACACCACGCCGAATATTAACATCAACA

ATGGTAACATTACCGCACCGCCGTTTGGCCTGAACAGCGTGATTACGCCGAACCT

GTTTCCGGGTGTTAGCATCTCTGCCCGTCTGGGCAATGGTCCGGGCATTCAAGAA

GTGGCAACCTTTAGTGTGCGCGTTTCCGGCGCTAAAGGCGGTGTCGCGGTGTCTA

ACGCCCACGGTACCGTTACGGGCGCGGCCGGCGGTGTCCTGCTGCGTCCGTTCGC

GCGCCTGATTGCCTCTACCGGCGACAGCGTTACGACCTATGGCGAACCGTGGAA

TATGAACTAA

Seq ID 4: MS-(B2)8 = MS-(L88N/D90N/D91N/D93N/D118R/D134R/
E139K)8
GLDNELSLVDGQDRTLTVQQWDTFLNGVFPLDRNRLTREWFHSGRAKYIVAGPGA

DEFEGTLELGYQIGFPWSLGVGINFSYTTPNININNGNITAPPFGLNSVITPNLFPGVSIS

ARLGNGPGIQEVATFSVRVSGAKGGVAVSNAHGTVTGAAGGVLLRPFARLIASTGD

SVTTYGEPWNMN

Seq ID: 5 (WT EcoExo I):
MMNDGKQQSTFLFHDYETFGTHPALDRPAQFAAIRTDSEFNVIGEPEVFYCKPADDY

LPQPGAVLITGITPQEARAKGENEAAFAARIHSLFTVPKTCILGYNNVRFDDEVTRNIF

YRNFYDPYAWSWQHDNSRWDLLDVMRACYALRPEGINWPENDDGLPSFRLEHLTK

ANGIEHSNAHDAMADVYATIAMAKLVKTRQPRLFDYLFTHRNKHKLMALIDVPQM

KPLVHVSGMFGAWRGNTSWVAPLAWHPENRNAVIMVDLAGDISPLLELDSDTLRE

RLYTAKTDLGDNAAVPVKLVHINKCPVLAQANTLRPEDADRLGINRQHCLDNLKIL

RENPQVREKVVAIFAEAEPFTPSDNVDAQLYNGFFSDADRAAMKIVLETEPRNLPAL

DITFVDKRIEKLLFNYRARNFPGTLDYAEQQRWLEHRRQVFTPEFLQGYADELQML

VQQYADDKEKVALLKALWQYAEEIVSGSGHHHHHH

Seq ID: 6 (E. coli Exonuclease III):
MKFVSFNINGLRARPHQLEAIVEKHQPDVIGLQETKVHDDMFPLEEVAKLGYNVFY

HGQKGHYGVALLTKETPIAVRRGFPGDDEEAQRRIIMAEIPSLLGNVTVINGYFPQGE

SRDHPIKFPAKAQFYQNLQNYLETELKRDNPVLIMGDMNISPTDLDIGIGEENRKRW

LRTGKCSFLPEEREWMDRLMSWGLVDTFRHANPQTADRFSWFDYRSKGFDDNRGL

RIDLLLASQPLAECCVETGIDYEIRSMEKPSDHAPVWATFRR

Seq ID: 7 (T. thermophilus RecJ):
MRDRVRWRVLSLPPLAQWREVMAALEVGPEAALAYWHRGFRRKEDLDPPLALLPL

KGLREAAALLEEALRQGKRIRVHGDYDADGLTGTAILVRGLAALGADVHPFIPHRLE

EGYGVLMERVPEHLEASDLFLTVDCGITNHAELRELLENGVEVIVTDHHTPGKTPSP

GLVVHPALTPDLKEKPTGAGVVFLLLWALHERLGLPPPLEYADLAAVGTIADVAPL

WGWNRALVKEGLARIPASSWVGLRLLAEAVGYTGKAVEVAFRIAPRINAASRLGEA

EKALRLLLTDDAAEAQALVGELHRLNARRQTLEEAMLRKLLPQADPEAKAIVLLDP

EGHPGVMGIVASRILEATLRPVFLVAQGKGTVRSLAPISAVEALRSAEDLLLRYGGH

KEAAGFAMDEALFPAFKARVEAYAARFPDPVREVALLDLLPEPGLLPQVFRELALLE

PYGEGNPEPLFLLFGAPEEARRLGEGRHLAFRLKGVRVLAWKQGDLALPPEVEVAG

LLSENAWNGHLAYEVQAVDLRKPEALEGGIAPFAYPLPLLEALARARLGEGVYVPE

DNPEGLDYARKAGFRLLPPEEAGLWLGLPPRPVLGRRVEVALGREARARLSAPPVL

HTPEARLKALVHRRLLFAYERRHPGLFSEALLAYWEVNRVQEPAGSP

Seq ID: 8 (Lambda Exonuclease):
MTPDIILQRTGIDVRAVEQGDDAWHKLRLGVITASEVHNVIAKPRSGKKWPDMKMS

YFHTLLAEVCTGVAPEVNAKALAWGKQYENDARTLFEFTSGVNVTESPIIYRDESM

RTACSPDGLCSDGNGLELKCPFTSRDFMKFRLGGFEAIKSAYMAQVQYSMWVTRK

NAWYFANYDPRMKREGLHYVVIERDEKYMASFDEIVPEFIEKMDEALAEIGFVFGE

QWR

Seq ID: 9 (Phi29 DNA polymerase):
MKHMPRKMYSCAFETTTKVEDCRVWAYGYMNIEDHSEYKIGNSLDEFMAWVLKV

QADLYFHNLKFDGAFIINWLERNGFKWSADGLPNTYNTIISRMGQWYMIDICLGYK

GKRKIHTVIYDSLKKLPFPVKKIAKDFKLTVLKGDIDYHKERPVGYKITPEEYAYIKN

DIQIIAEALLIQFKQGLDRMTAGSDSLKGFKDIITTKKFKKVFPTLSLGLDKEVRYAYR

GGFTWLNDRFKEKEIGEGMVFDVNSLYPAQMYSRLLPYGEPIVFEGKYVWDEDYPL

HIQHIRCEFELKEGYIPTIQIKRSRFYKGNEYLKSSGGEIADLWLSNVDLELMKEHYD

LYNVEYISGLKFKATTGLFKDFIDKWTYIKTTSEGAIKQLAKLMLNSLYGKFASNPD

VTGKVPYLKENGALGFRLGEEETKDPVYTPMGVFITAWARYTTITAAQACYDRIIYC

DTDSIHLTGTEIPDVIKDIVDPKKLGYWAHES TFKRAKYLRQKTYIQDIYMKEVDGK

LVEGSPDDYTDIKFSVKCAGMTDKIKKEVTFENFKVGFSRKMKPKPVQVPGGVVLV

DDTFTIKSGGSAWSHPQFEKGGGSGGGSGGSAWSHPQFEK

The invention claimed is:

1. A method of controlling a biochemical analysis system, the method comprising:

analyzing a series of measurements obtained from a portion of a first polymer that is partially translocated through a nanopore of the biochemical analysis system, and reference data derived from at least one reference sequence of polymer units, wherein the first polymer is a polynucleotide, and the series of measurements is obtained from around 30 nucleotides to about 250 nucleotides of the first polymer;

providing a measure of similarity during translocation between the analyzed series of measurements and the reference data; and operating the biochemical analysis system to eject the first polymer from the nanopore responsive to the measure of similarity; wherein (i) at least one sensor element is operable to eject a polymer that is translocating through the nanopore, and the step of operating the biochemical analysis system to eject the first polymer from the nanopore comprises operating the sensor element to eject the first polymer from the nanopore and accept a further polymer in the nanopore and taking measurements from the further polymer, wherein the further polymer is a polynucleotide; or (ii) the biochemical analysis system comprises an array of sensor elements and is operable to take successive measurements of a polymer from sensor elements selected in an electrically multiplexed manner, and the step of operating the biochemical analysis system to eject the first polymer from the nanopore comprises operating the biochemical analysis system to cease taking measurements from a currently selected sensor element and to start taking measurements of a further polymer from a newly selected sensor element, wherein the further polymer is a polynucleotide.

2. The method according to claim 1, further comprising obtaining the series of measurements from the first polymer during the partial translocation.

3. The method according to claim 1, wherein the series of measurements is obtained by taking successive measurements of the polymer as it translocates through the nanopore.

4. The method according to claim 3, wherein the successive measurements comprise one or more groups of plural measurements that are dependent on a single k-mer without a priori knowledge of the number of measurements in each group.

5. The method according to claim 1, wherein analyzing the series of measurements and the reference data to provide the measure of similarity comprises using a distance function to provide, as the measure of similarity, a measure of the distance between the series of measurements and the reference data.

6. The method according to claim 1, wherein the nanopore is a biological pore.

7. A computer-implemented method of controlling a biochemical analysis system, the method comprising the method according to claim 1.

8. The method of claim 1, wherein the series of measurements is a series of electrical measurements.

9. The method according to claim 1, wherein the measurements are raw measurements, wherein the raw measurements are electrical measurements or optical measurements or a combination thereof.

* * * * *

UNITED STATES PATENT AND TRADEMARK OFFICE
CERTIFICATE OF CORRECTION

PATENT NO. : 11,401,549 B2
APPLICATION NO. : 15/930198
DATED : August 2, 2022
INVENTOR(S) : Stuart William Reid et al.

It is certified that error appears in the above-identified patent and that said Letters Patent is hereby corrected as shown below:

On the Title Page

Item (30) Foreign Application Priority Data should read:
Oct. 16, 2014 (GB) .................................... 1418366.9
Oct. 16, 2014 (GB) .................................... 1418379.2
May 6, 2015 (GB) .................................... 1507742.3

Item (57) ABSTRACT should read:
A biochemical analysis system analyses polymers by taking measurements of a polymer from a sensor element comprising a nanopore during translocation of the polymer through the nanopore. When a polymer has partially translocated, the series of measurements is analysed using reference data derived from a reference sequence to provide a measure of similarity. Responsive to the measure of similarity, the sensor element may be selectively operated to eject the polymer and thereby make the nanopore available to receive a further polymer. Where the biochemical analysis system comprises an array of sensor elements and takes measurements from sensor elements selected in a multiplexed manner, responsive to the measure of similarity, the biochemical analysis system ceases taking measurements from the currently selected sensor element and starts taking measurements from a newly selected sensor element.

Signed and Sealed this
Twenty-fifth Day of October, 2022

Katherine Kelly Vidal
*Director of the United States Patent and Trademark Office*

SEQUENCE LISTING

<160> NUMBER OF SEQ ID NOS: 9

<210> SEQ ID NO 1
<211> LENGTH: 558
<212> TYPE: DNA
<213> ORGANISM: Artificial Sequence
<220> FEATURE:
<223> OTHER INFORMATION: Synthetic Polynucleotide

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 2
<211> LENGTH: 184
<212> TYPE: PRT
<213> ORGANISM: Artificial Sequence
<220> FEATURE:
<223> OTHER INFORMATION: Synthetic Polypeptide

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 558
<212> TYPE: DNA
<213> ORGANISM: Artificial Sequence
<220> FEATURE:
<223> OTHER INFORMATION: Synthetic Polynucleotide

<400> SEQUENCE: 3

```
atgggtctgg ataatgaact gagcctggtg acggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattaacatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 4
<211> LENGTH: 184
<212> TYPE: PRT
<213> ORGANISM: Artificial Sequence
<220> FEATURE:
<223> OTHER INFORMATION: Synthetic Polypeptide

<400> SEQUENCE: 4

```
Gly Leu Asp Asn Glu Leu Ser Leu Val Asp Gly Gln Asp Arg Thr Leu
1               5                   10                  15
Thr Val Gln Gln Trp Asp Thr Phe Leu Asn Gly Val Phe Pro Leu Asp
            20                  25                  30
Arg Asn Arg Leu Thr Arg Glu Trp Phe His Ser Gly Arg Ala Lys Tyr
        35                  40                  45
Ile Val Ala Gly Pro Gly Ala Asp Glu Phe Glu Gly Thr Leu Glu Leu
    50                  55                  60
Gly Tyr Gln Ile Gly Phe Pro Trp Ser Leu Gly Val Gly Ile Asn Phe
65                  70                  75                  80
Ser Tyr Thr Thr Pro Asn Ile Asn Ile Asn Asn Gly Asn Ile Thr Ala
                85                  90                  95
Pro Pro Phe Gly Leu Asn Ser Val Ile Thr Pro Asn Leu Phe Pro Gly
            100                 105                 110
Val Ser Ile Ser Ala Arg Leu Gly Asn Gly Pro Gly Ile Gln Glu Val
        115                 120                 125
Ala Thr Phe Ser Val Arg Val Ser Gly Ala Lys Gly Gly Val Ala Val
    130                 135                 140
Ser Asn Ala His Gly Thr Val Thr Gly Ala Ala Gly Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
            180
```

<210> SEQ ID NO 5
<211> LENGTH: 485
<212> TYPE: PRT

<213> ORGANISM: Escherichia coli

<400> SEQUENCE: 5

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

```
Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
450                 455                 460

Lys Ala Leu Trp Gln Tyr Ala Glu Glu Ile Val Ser Gly Ser Gly His
465                 470                 475                 480

His His His His His
                485

<210> SEQ ID NO 6
<211> LENGTH: 268
<212> TYPE: PRT
<213> ORGANISM: Escherichia coli

<400> SEQUENCE: 6

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265

<210> SEQ ID NO 7
```

<211> LENGTH: 666
<212> TYPE: PRT
<213> ORGANISM: Thermus thermophilus

<400> SEQUENCE: 7

Met Arg Asp Arg Val Arg Trp Arg Val Leu Ser Leu Pro Pro Leu Ala
1               5                   10                  15

Gln Trp Arg Glu Val Met Ala Ala Leu Glu Val Gly Pro Glu Ala Ala
            20                  25                  30

Leu Ala Tyr Trp His Arg Gly Phe Arg Arg Lys Glu Asp Leu Asp Pro
        35                  40                  45

Pro Leu Ala Leu Leu Pro Leu Lys Gly Leu Arg Glu Ala Ala Ala Leu
50                  55                  60

Leu Glu Glu Ala Leu Arg Gln Gly Lys Arg Ile Arg Val His Gly Asp
65                  70                  75                  80

Tyr Asp Ala Asp Gly Leu Thr Gly Thr Ala Ile Leu Val Arg Gly Leu
                85                  90                  95

Ala Ala Leu Gly Ala Asp Val His Pro Phe Ile Pro His Arg Leu Glu
            100                 105                 110

Glu Gly Tyr Gly Val Leu Met Glu Arg Val Pro Glu His Leu Glu Ala
        115                 120                 125

Ser Asp Leu Phe Leu Thr Val Asp Cys Gly Ile Thr Asn His Ala Glu
130                 135                 140

Leu Arg Glu Leu Leu Glu Asn Gly Val Glu Val Ile Val Thr Asp His
145                 150                 155                 160

His Thr Pro Gly Lys Thr Pro Ser Pro Gly Leu Val Val His Pro Ala
                165                 170                 175

Leu Thr Pro Asp Leu Lys Glu Lys Pro Thr Gly Ala Gly Val Val Phe
            180                 185                 190

Leu Leu Leu Trp Ala Leu His Glu Arg Leu Gly Leu Pro Pro Pro Leu
        195                 200                 205

Glu Tyr Ala Asp Leu Ala Ala Val Gly Thr Ile Ala Asp Val Ala Pro
210                 215                 220

Leu Trp Gly Trp Asn Arg Ala Leu Val Lys Glu Gly Leu Ala Arg Ile
225                 230                 235                 240

Pro Ala Ser Ser Trp Val Gly Leu Arg Leu Leu Ala Glu Ala Val Gly
                245                 250                 255

Tyr Thr Gly Lys Ala Val Glu Val Ala Phe Arg Ile Ala Pro Arg Ile
            260                 265                 270

Asn Ala Ala Ser Arg Leu Gly Glu Ala Glu Lys Ala Leu Arg Leu Leu
        275                 280                 285

Leu Thr Asp Asp Ala Ala Glu Ala Gln Ala Leu Val Gly Glu Leu His
290                 295                 300

Arg Leu Asn Ala Arg Arg Gln Thr Leu Glu Glu Ala Met Leu Arg Lys
305                 310                 315                 320

Leu Leu Pro Gln Ala Asp Pro Glu Ala Lys Ala Ile Val Leu Leu Asp
                325                 330                 335

Pro Glu Gly His Pro Gly Val Met Gly Ile Val Ala Ser Arg Ile Leu
            340                 345                 350

Glu Ala Thr Leu Arg Pro Val Phe Leu Val Ala Gln Gly Lys Gly Thr
        355                 360                 365

Val Arg Ser Leu Ala Pro Ile Ser Ala Val Glu Ala Leu Arg Ser Ala
370                 375                 380

Glu Asp Leu Leu Leu Arg Tyr Gly Gly His Lys Glu Ala Ala Gly Phe

```
                385                 390                 395                 400
        Ala Met Asp Glu Ala Leu Phe Pro Ala Phe Lys Ala Arg Val Glu Ala
                        405                 410                 415

Tyr Ala Ala Arg Phe Pro Asp Pro Val Arg Glu Val Ala Leu Leu Asp
                        420                 425                 430

Leu Leu Pro Glu Pro Gly Leu Leu Pro Gln Val Phe Arg Glu Leu Ala
                        435                 440                 445

Leu Leu Glu Pro Tyr Gly Glu Gly Asn Pro Gly Pro Leu Phe Leu Leu
                        450                 455                 460

Phe Gly Ala Pro Glu Glu Ala Arg Arg Leu Gly Glu Gly Arg His Leu
        465                 470                 475                 480

Ala Phe Arg Leu Lys Gly Val Arg Val Leu Ala Trp Lys Gln Gly Asp
                        485                 490                 495

Leu Ala Leu Pro Pro Glu Val Glu Val Ala Gly Leu Leu Ser Glu Asn
                        500                 505                 510

Ala Trp Asn Gly His Leu Ala Tyr Glu Val Gln Ala Val Asp Leu Arg
                        515                 520                 525

Lys Pro Glu Ala Leu Glu Gly Gly Ile Ala Pro Phe Ala Tyr Pro Leu
                        530                 535                 540

Pro Leu Leu Glu Ala Leu Ala Arg Ala Arg Leu Gly Glu Gly Val Tyr
        545                 550                 555                 560

Val Pro Glu Asp Asn Pro Glu Gly Leu Asp Tyr Ala Arg Lys Ala Gly
                        565                 570                 575

Phe Arg Leu Leu Pro Pro Glu Glu Ala Gly Leu Trp Leu Gly Leu Pro
                        580                 585                 590

Pro Arg Pro Val Leu Gly Arg Arg Val Glu Val Ala Leu Gly Arg Glu
                        595                 600                 605

Ala Arg Ala Arg Leu Ser Ala Pro Pro Val Leu His Thr Pro Glu Ala
                        610                 615                 620

Arg Leu Lys Ala Leu Val His Arg Arg Leu Leu Phe Ala Tyr Glu Arg
        625                 630                 635                 640

Arg His Pro Gly Leu Phe Ser Glu Ala Leu Leu Ala Tyr Trp Glu Val
                        645                 650                 655

Asn Arg Val Gln Glu Pro Ala Gly Ser Pro
                        660                 665

<210> SEQ ID NO 8
<211> LENGTH: 226
<212> TYPE: PRT
<213> ORGANISM: Bacteriophage lambda

<400> SEQUENCE: 8

Met Thr Pro Asp Ile Ile Leu Gln Arg Thr Gly Ile Asp Val Arg Ala
        1               5                   10                  15

Val Glu Gln Gly Asp Asp Ala Trp His Lys Leu Arg Leu Gly Val Ile
                        20                  25                  30

Thr Ala Ser Glu Val His Asn Val Ile Ala Lys Pro Arg Ser Gly Lys
                        35                  40                  45

Lys Trp Pro Asp Met Lys Met Ser Tyr Phe His Thr Leu Leu Ala Glu
                        50                  55                  60

Val Cys Thr Gly Val Ala Pro Glu Val Asn Ala Lys Ala Leu Ala Trp
        65                  70                  75                  80

Gly Lys Gln Tyr Glu Asn Asp Ala Arg Thr Leu Phe Glu Phe Thr Ser
                        85                  90                  95
```

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
            115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 9
<211> LENGTH: 608
<212> TYPE: PRT
<213> ORGANISM: Bacteriophage phi-29

<400> SEQUENCE: 9

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

-continued

```
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
                260                 265                 270
Gly Lys Tyr Val Trp Asp Glu Asp Tyr Pro Leu His Ile Gln His Ile
                275                 280                 285
Arg Cys Glu Phe Glu Leu Lys Glu Gly Tyr Ile Pro Thr Ile Gln Ile
                290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Glu Gly Ala Ile Lys Gln Leu Ala Lys Leu
                370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
                420                 425                 430
Ile Thr Ala Trp Ala Arg Tyr Thr Thr Ile Thr Ala Ala Gln Ala Cys
                435                 440                 445
Tyr Asp Arg Ile Ile Tyr Cys Asp Thr Asp Ser Ile His Leu Thr Gly
                450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
                500                 505                 510
Leu Val Glu Gly Ser Pro Asp Asp Tyr Thr Asp Ile Lys Phe Ser Val
                515                 520                 525
Lys Cys Ala Gly Met Thr Asp Lys Ile Lys Lys Glu Val Thr Phe Glu
                530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys Ser
                565                 570                 575
Gly Gly Ser Ala Trp Ser His Pro Gln Phe Glu Lys Gly Gly Gly Ser
                580                 585                 590
Gly Gly Gly Ser Gly Gly Ser Ala Trp Ser His Pro Gln Phe Glu Lys
                595                 600                 605
```